(12) United States Patent
Chambers et al.

(10) Patent No.: US 10,241,117 B2
(45) Date of Patent: *Mar. 26, 2019

(54) METHODS FOR QUANTIFYING POLYPEPTIDES USING MASS SPECTROMETRY

(71) Applicant: Waters Technologies Corporation, Milford, MA (US)

(72) Inventors: Erin E. Chambers, North Brookfield, MA (US); Martha Stapels, Bellingham, MA (US); Joanne Mather, Millis, MA (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/965,613

(22) Filed: Apr. 27, 2018

(65) Prior Publication Data

US 2018/0246119 A1    Aug. 30, 2018

Related U.S. Application Data

(63) Continuation of application No. 15/447,838, filed on Mar. 2, 2017, now Pat. No. 9,964,545, which is a continuation of application No. 14/394,952, filed as application No. PCT/US2013/031595 on Mar. 14, 2013, now Pat. No. 9,588,130.

(60) Provisional application No. 61/740,973, filed on Dec. 21, 2012, provisional application No. 61/649,404, filed on May 21, 2012, provisional application No. 61/635,013, filed on Apr. 18, 2012.

(51) Int. Cl.
| *G01N 33/68* | (2006.01) |
| *G01N 33/74* | (2006.01) |
| *G01N 33/02* | (2006.01) |
| *G01N 30/72* | (2006.01) |
| *G01N 30/86* | (2006.01) |
| *G01N 30/88* | (2006.01) |

(52) U.S. Cl.
CPC ..... *G01N 33/6848* (2013.01); *G01N 30/7233* (2013.01); *G01N 30/7266* (2013.01); *G01N 30/8679* (2013.01); *G01N 30/88* (2013.01); *G01N 33/74* (2013.01); *G01N 33/02* (2013.01); *G01N 2030/8831* (2013.01); *Y10T 436/24* (2015.01)

(58) Field of Classification Search
CPC .... G01N 30/02; G01N 30/72; G01N 30/7233; G01N 30/7266; G01N 30/86; G01N 30/8679; G01N 30/88; G01N 2030/8831; G01N 33/68; G01N 33/6848; G01N 33/74; G01N 33/02; Y10T 436/24; Y10T 436/25; Y10T 436/25375; Y10T 436/255
USPC .... 436/86, 161, 173, 174, 177, 178; 422/70, 422/527

See application file for complete search history.

(56) References Cited

U.S. PATENT DOCUMENTS

| 9,588,130 B2 | 3/2017 | Chambers et al. |
| 9,964,545 B2 * | 5/2018 | Chambers .......... G01N 33/6848 |
| 2003/0144181 A1 | 7/2003 | Brader |
| 2007/0015158 A1 | 1/2007 | McLuckey et al. |
| 2007/0087448 A1 | 4/2007 | Nelsestuen |
| 2009/0173876 A1 | 7/2009 | Li et al. |
| 2009/0192075 A1 | 7/2009 | Steiner |
| 2011/0022326 A1 | 1/2011 | Oda et al. |
| 2011/0111512 A1 | 5/2011 | Bystrom et al. |
| 2011/0301081 A1 | 12/2011 | Becker et al. |
| 2012/0164741 A1 | 6/2012 | Chen et al. |

OTHER PUBLICATIONS

Chambers et al. Journal of Chromatography B, vol. 938, Sep. 3, 2013, pp. 96-104.
Lucie et al. "Evaluation of new mixed-mode UHPLC stationary phases and the importance of stationary phase choice when using low ionic-strength mobile Iphase additives" Talanta, vol. 93, Feb. 3, 2012, pp. 99-105.
Lame et al. Analytical Biochemistry, vol. 419, Aug. 12, 2011, pp. 133-139.
The International Search Report and The Written Opinion of the International Search Authority in the Application No. PCT/US13/31595, dated May 28, 2013.

* cited by examiner

*Primary Examiner* — Maureen Wallenhorst
(74) *Attorney, Agent, or Firm* — Womble Bond Dickinson (US) LLP; Deborah M. Vernon; Rebecca N. Barnes

(57) ABSTRACT

A method for identifying a polypeptide a specimen can include (i) treating a specimen suspected of including an insulin with a base; (ii) extracting a first fraction of the treated specimen by solid phase extraction using a mixed mode or polymeric reversed-phase media and a first solvent including an acid; (iii) separating a component of the first fraction by liquid chromatography using a chromatographic surface including a hydrophobic surface group and one or more ionizable modifiers, and a second solvent including an acid; and (iv) analyzing the component of the first fraction by mass spectroscopy, thereby identifying the polypeptide, if present, using a signal corresponding to a sequence fragment ion from the polypeptide. The signal can correspond to an intact multiply charged precursor fragment selected in a first quadrupole and its corresponding sequence fragment ion selected in a final quadrupole.

28 Claims, 27 Drawing Sheets

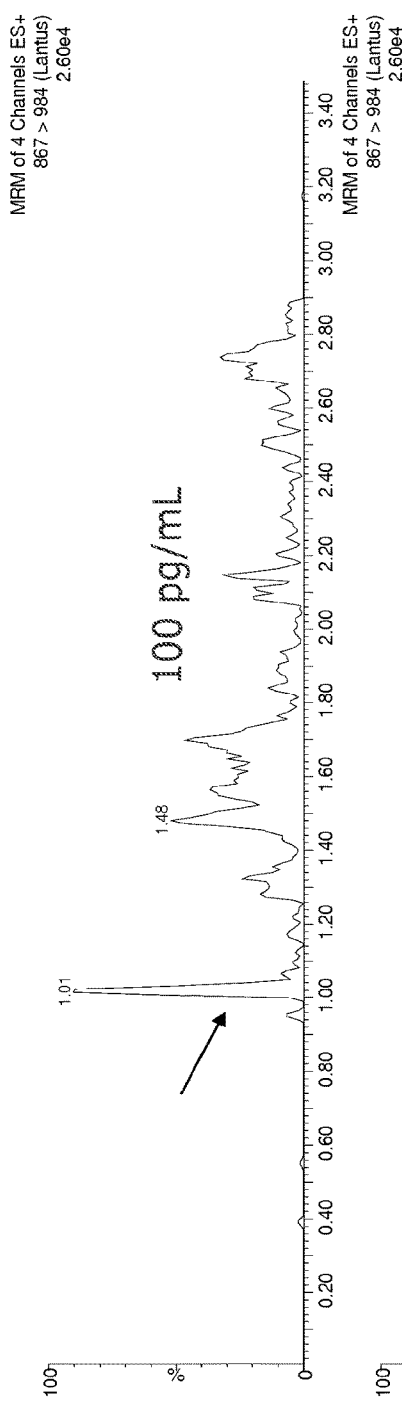
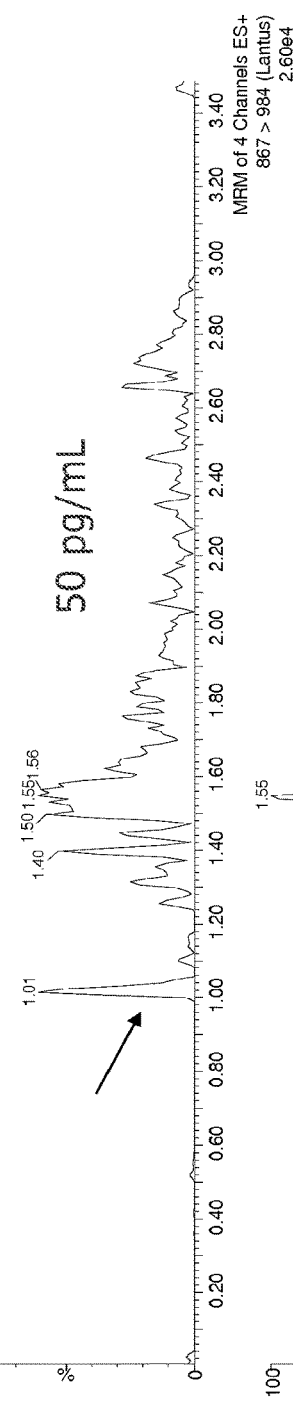
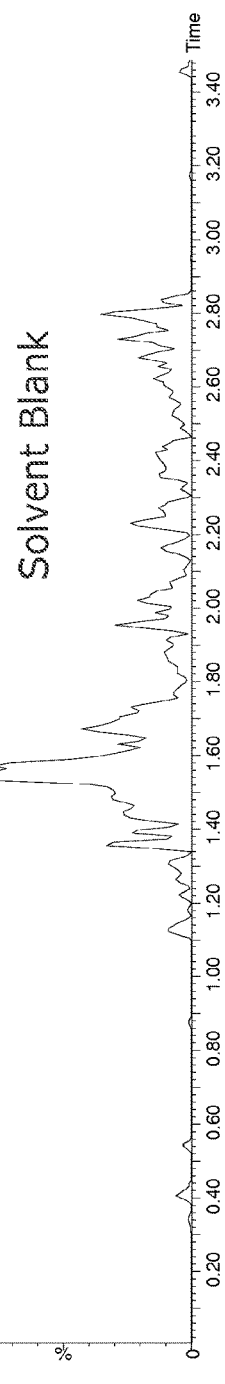
FIG. 4A
FIG. 4B
FIG. 4C

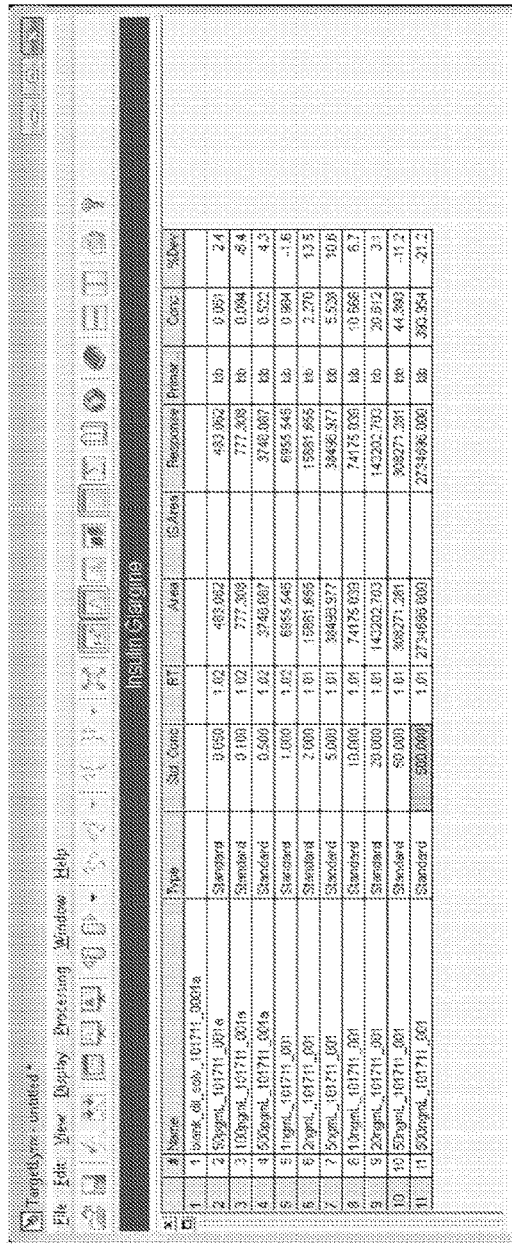
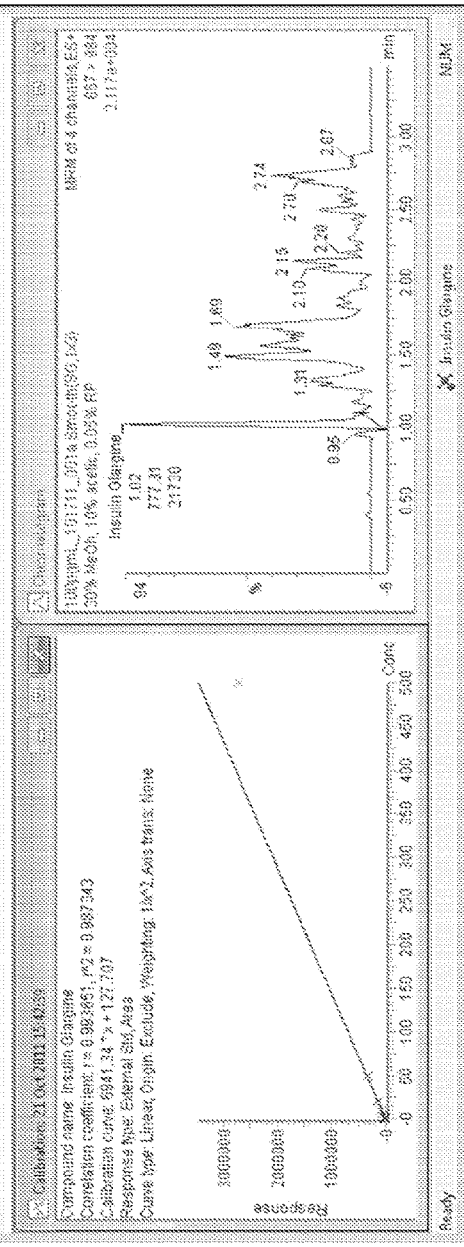
FIG. 5A
FIG. 5B
FIG. 5C

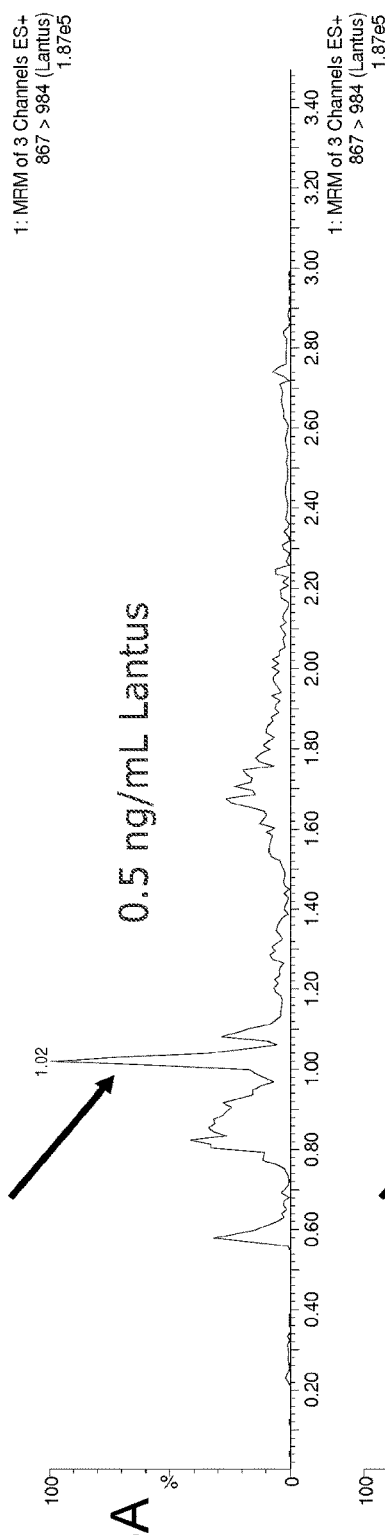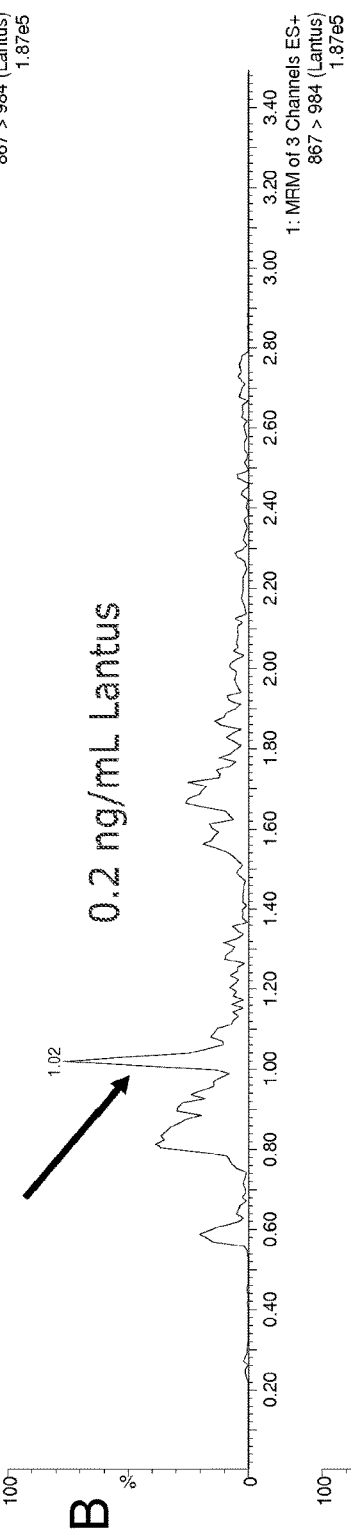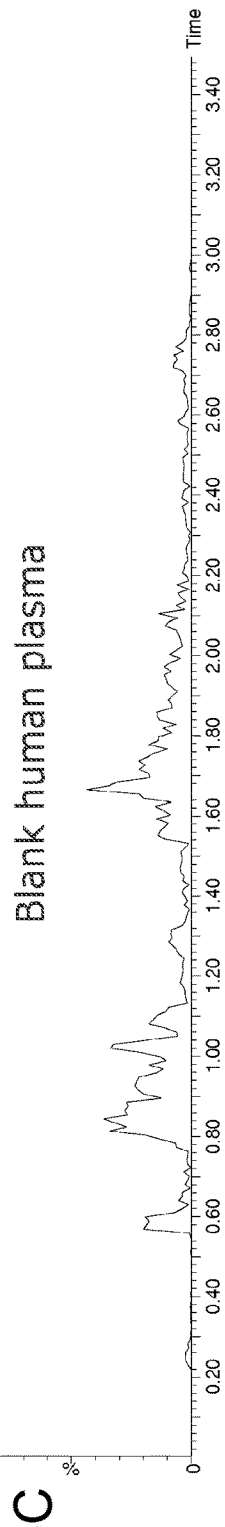
FIG. 6A
FIG. 6B
FIG. 6C

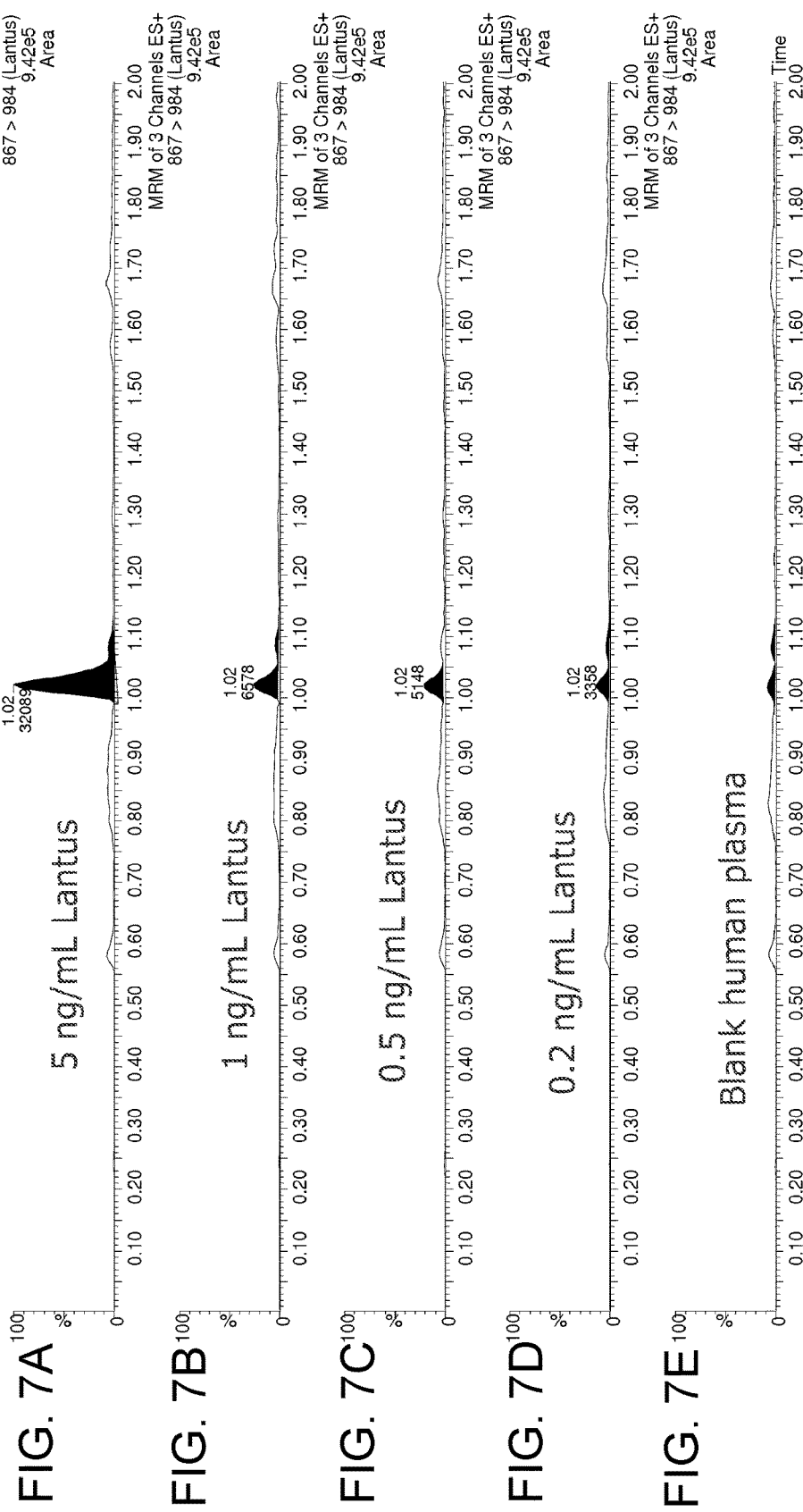

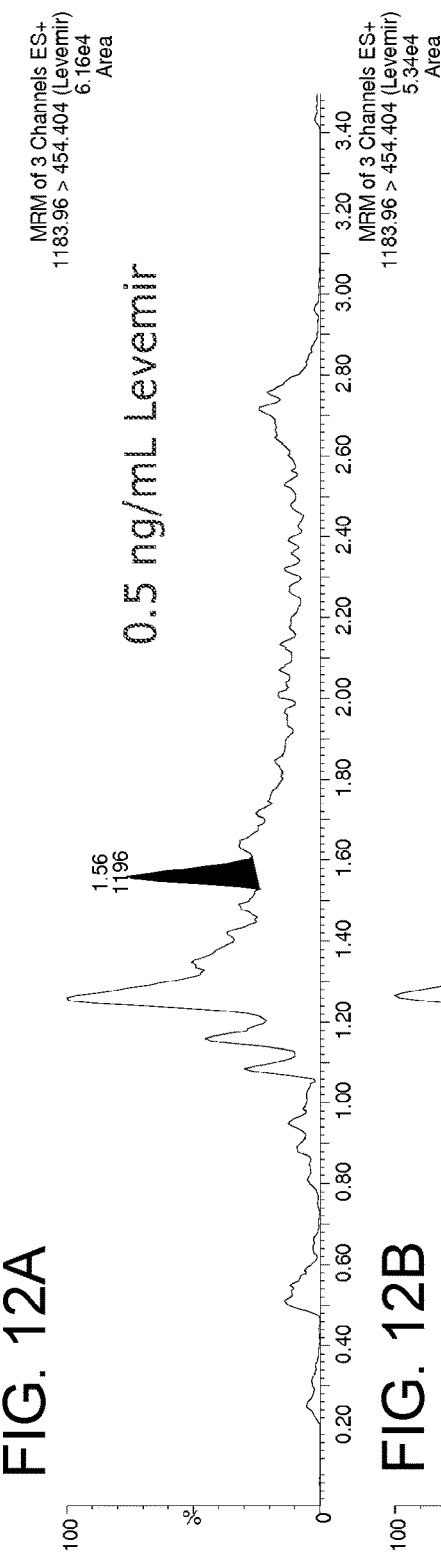
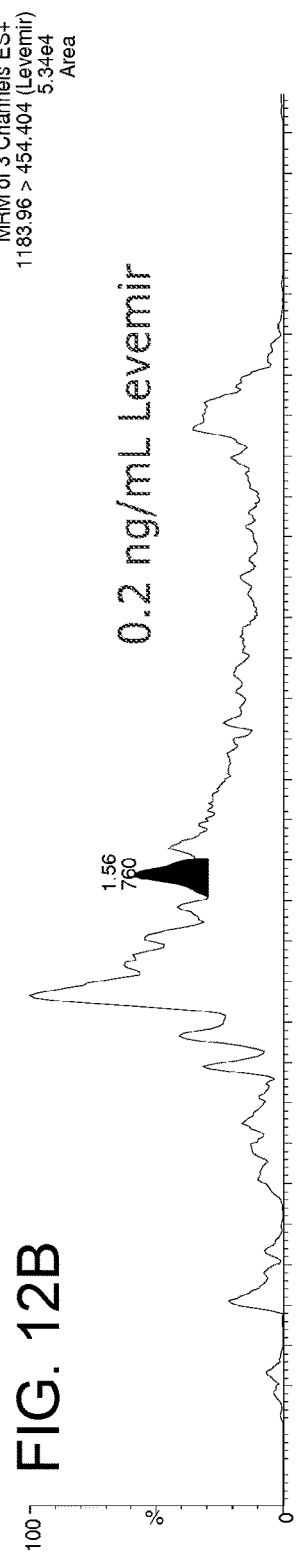
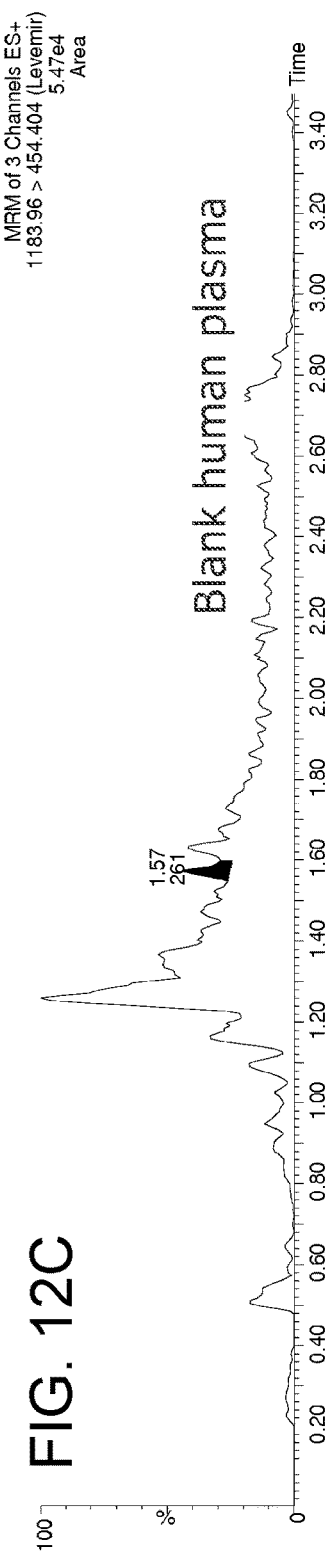
FIG. 12A  0.5 ng/mL Levemir
FIG. 12B  0.2 ng/mL Levemir
FIG. 12C  Blank human plasma

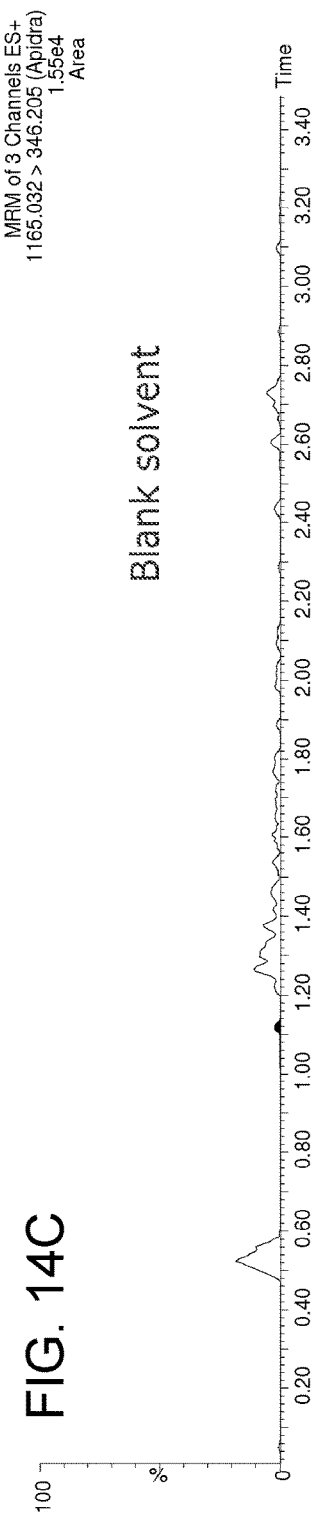
FIG. 14A  100 pg/mL Apidra
FIG. 14B  50 pg/mL Apidra
FIG. 14C  Blank solvent

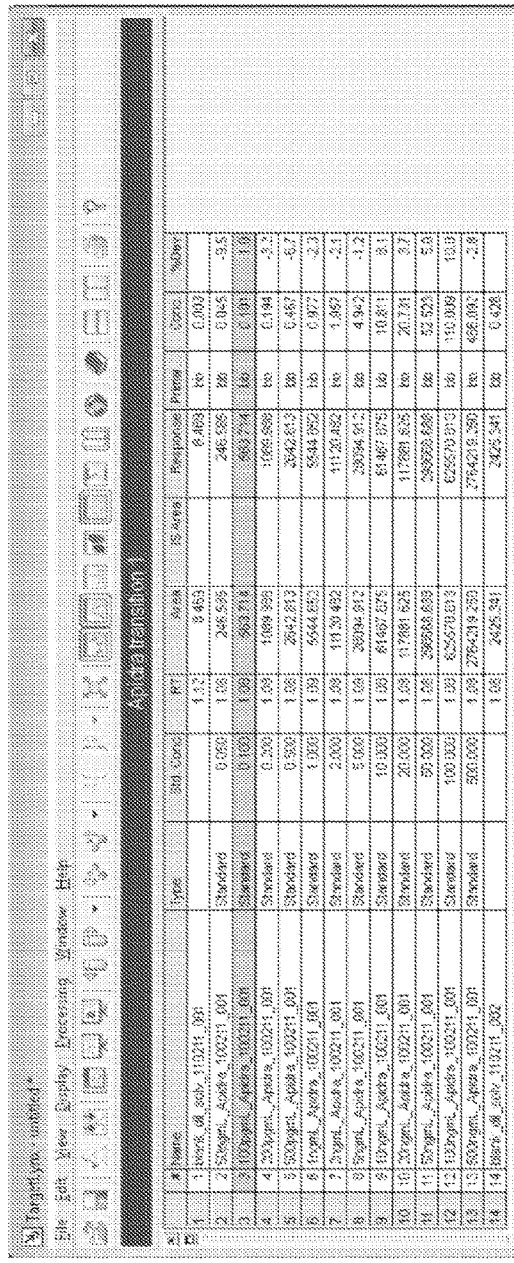
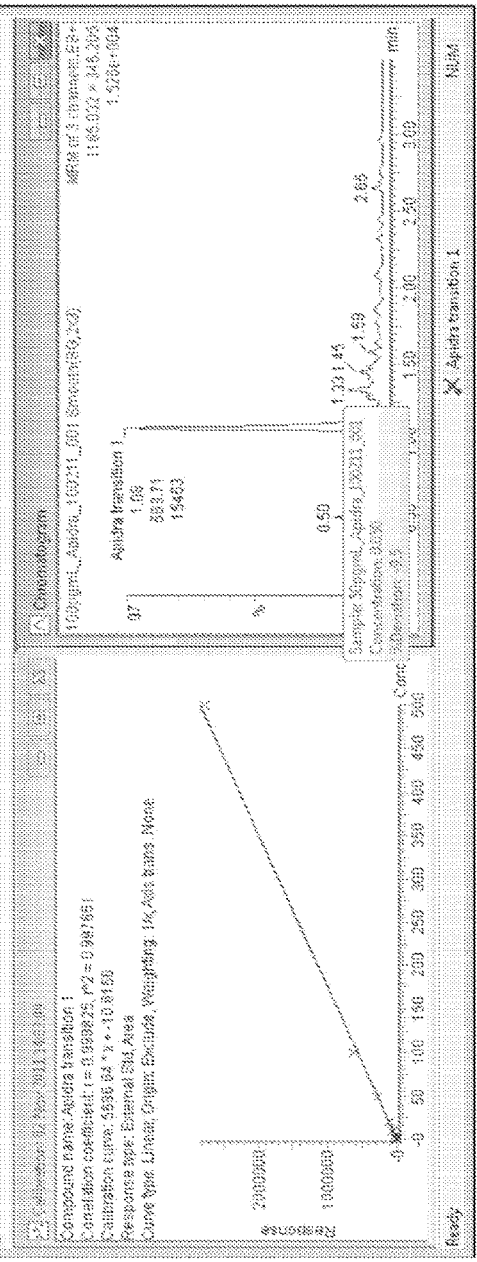
FIG. 15A
FIG. 15B
FIG. 15C

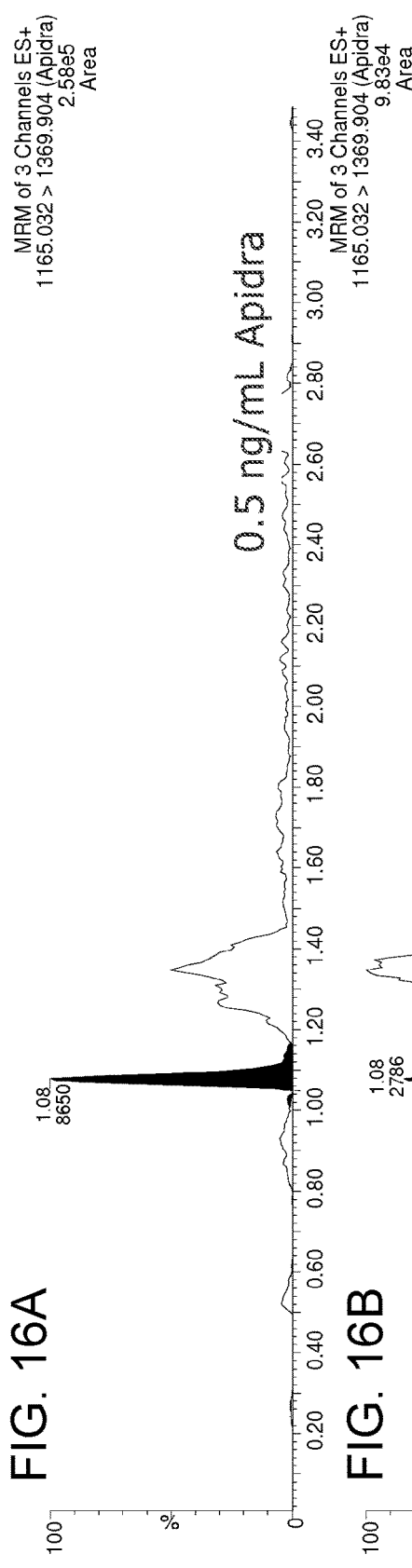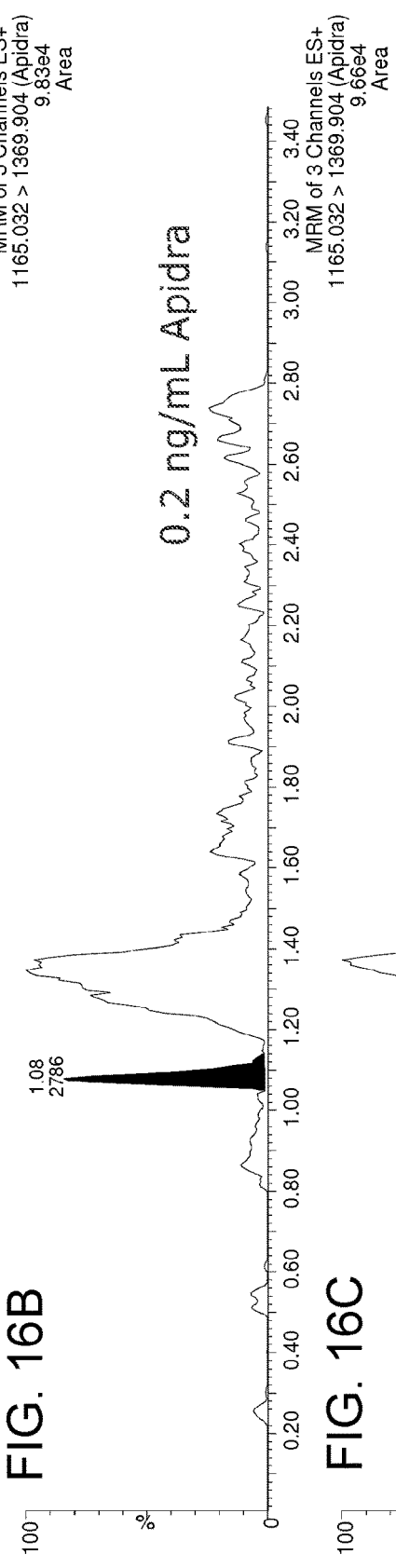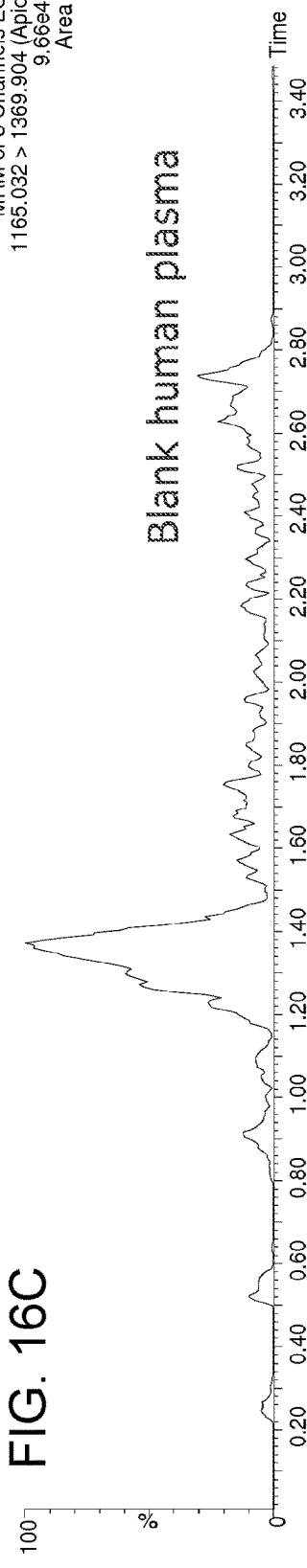

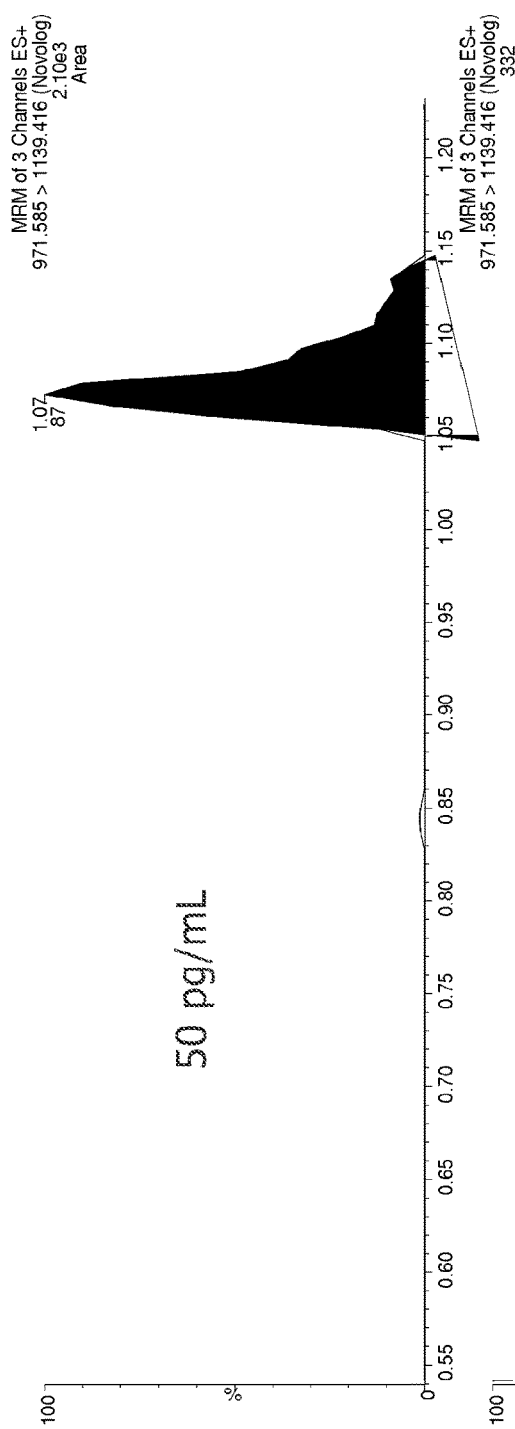
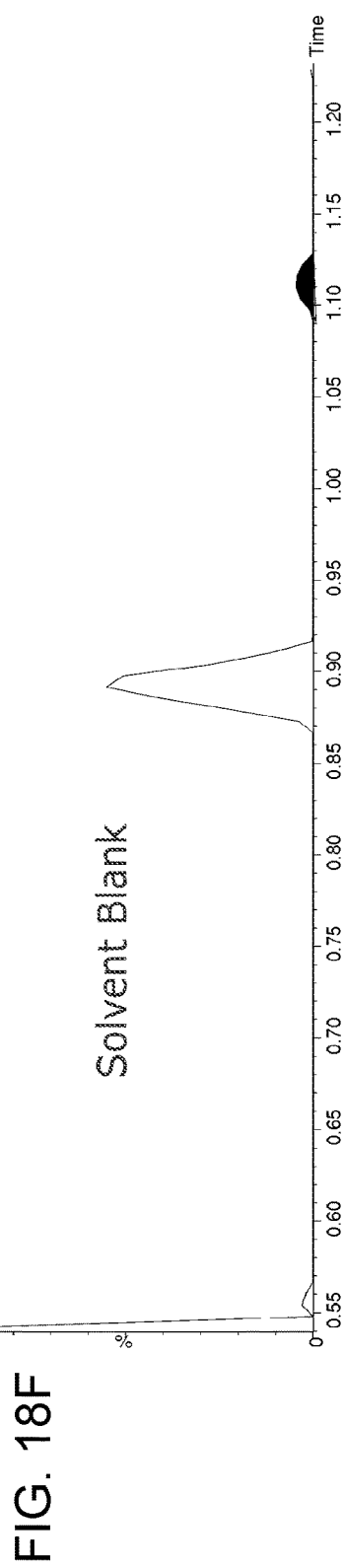
FIG. 18E
FIG. 18F

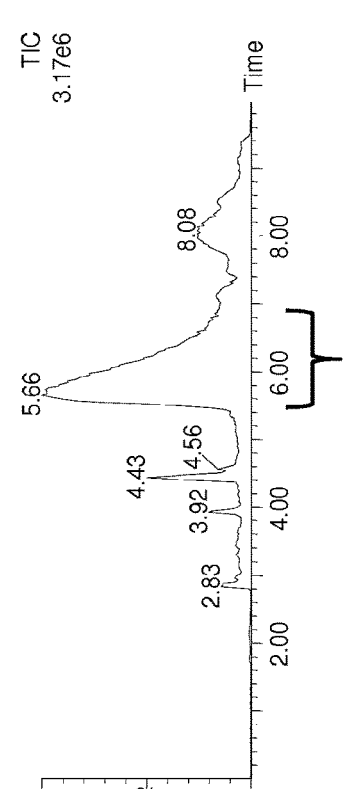
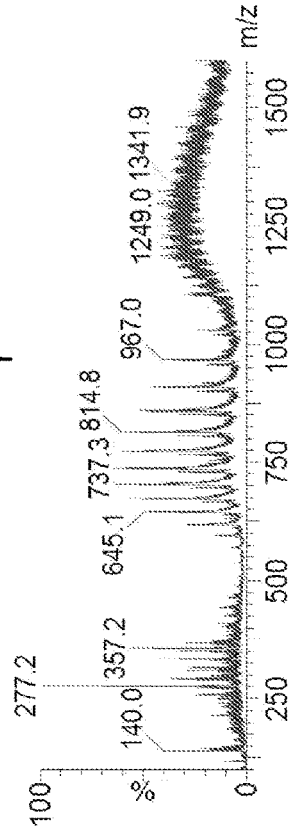
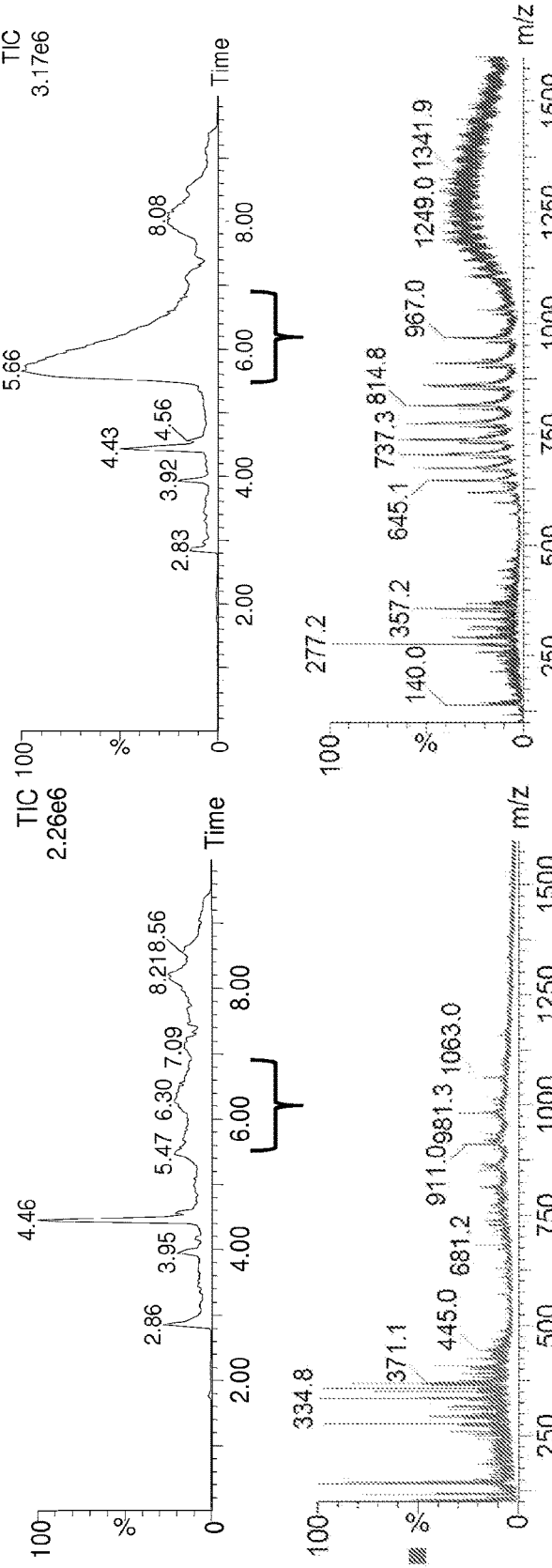
FIG. 21A TRIS base pretreatment
FIG. 21B
FIG. 21C TFA pretreatment
FIG. 21D

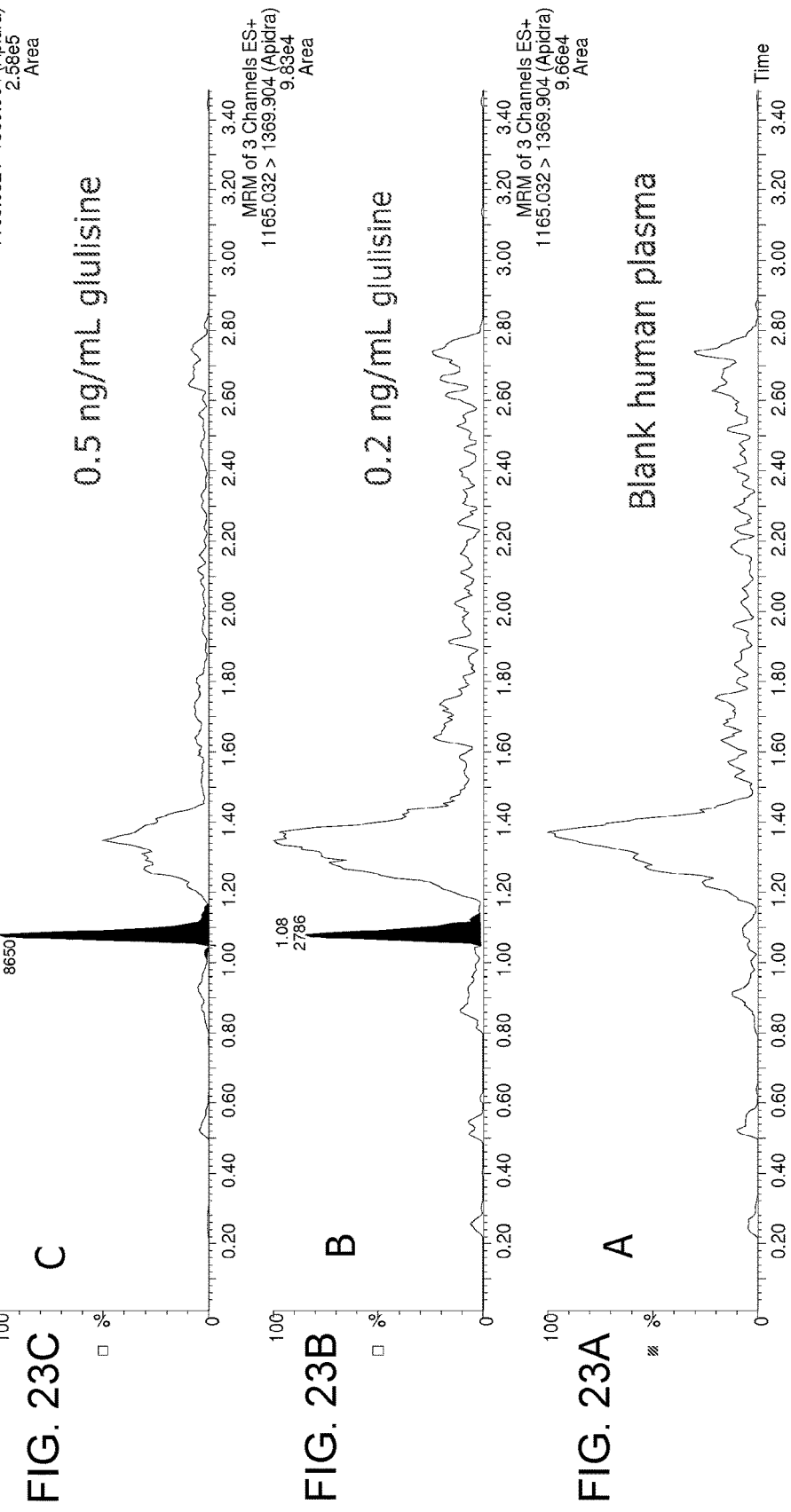

METHODS FOR QUANTIFYING POLYPEPTIDES USING MASS SPECTROMETRY

RELATED APPLICATIONS

This application is a continuation of U.S. utility application Ser. No. 15/447,838, filed on Mar. 2, 2017, and will issue as U.S. Pat. No. 9,964,545 on May 8, 2018. U.S. utility application Ser. No. 15/447,838 is a continuation of U.S. utility application Ser. No. 14/394,952, filed on Oct. 16, 2014, and issued as U.S. Pat. No. 9,588,130 on Mar. 7, 2017. U.S. utility application Ser. No. 14/394,952 is a National Stage Application of International Application No. PCT/US2013/031595, filed Mar. 14, 2013, which claims priority to U.S. Provisional Application Nos. 61/635,013, filing date Apr. 18, 2012; 61/649,404, filing date May 21, 2012; and 61/740,973, filing date Dec. 21, 2012. Each of the foregoing applications is, incorporated herein by reference in its entirety.

FIELD OF THE TECHNOLOGY

The technology relates generally to methods for quantifying one or more polypeptides in a sample by mass spectrometry. The technology relates more particularly, in various embodiments, to combinations of mixed-mode or reversed-phase solid phase extraction, liquid chromatography including use of a chromatographic surface having a hydrophobic surface group and one or more ionizable modifiers, and high sensitivity mass spectroscopy for quantification of polypeptides.

BACKGROUND OF THE TECHNOLOGY

Polypeptides are commonly analyzed using ligand binding assays (LBA) such as enzyme-linked immunosorbent assays (ELISA). However, ELISA can lack specificity and accuracy, for example due to cross reactivity and an inability to distinguish similar molecules such as analogs and metabolites. Use of ligand binding assays such as ELISA for analyzing polypeptides is also hindered when suitable antibodies are not yet available for the polypeptide of interest. Development of antibodies can be an expensive and time-consuming process.

Although biologics have historically been quantified using ligand binding assays (LBAs), over the past few years, there has been a trend toward the analysis of large molecules by liquid chromatography tandem mass spectroscopy (LC-MS/MS). However, intact polypeptides such as insulin are particularly difficult to analyze by LC-MS/MS. For example, mass spectroscopy (MS) sensitivity can be low due to poor transfer into the gas phase and poor fragmentation due to the presence of multiple stabilizing disulfide bonds. In addition, polypeptides can suffer from non-specific binding and poor solubility, making liquid chromatography (LC) and sample preparation method development difficult.

SUMMARY OF THE TECHNOLOGY

In various aspects and embodiments, the technology includes methods for quantifying polypeptides by mass spectrometry, as well as corresponding compositions, kits, apparatuses, and the like. For example, the technology includes combinations of multi-step mixed-mode solid phase extraction, liquid chromatography column chemistry, wherein the chromatographic surface includes a hydrophobic surface group and one or more ionizable modifiers (e.g. a charged surface hybrid column, for instance an ACQUITY UPLC® CSH or XSelect™ column, commercially available from Waters Technology Corp., Milford, Mass.) and high sensitivity mass spectroscopy for quantification of polypeptides. The technology has numerous applications including polypeptide analysis, clinical diagnostics, medicine, biomarker and drug screening and discovery, bioequivalence testing, therapeutic monitoring, as well as related methods in food, industrial, and environmental fields.

For polypeptide analytes (e.g., insulins, which are heavily stabilized by disulfide bonds), it can be difficult to produce selective MS fragments because slight changes in collision energy result in little fragmentation, rapidly followed by extensive fragmentation into very small, non-specific fragments. The technology is well suited for studying such polypeptides. The technology is also generally applicable to quantifying large, low abundance peptides, mitigating non-specific binding, and/or mitigating evaporative losses in the analysis of polypeptides.

One advantageous feature of the technology addresses these issues by using a high sensitivity mass spectroscopy platform to produce specific polypeptide fragments. For example, triple quadrupole MS can be used to produce high m/z fragments that are analyte-specific (e.g., ranging from m/z 700-1400 in the example of insulin). Accordingly, the technology can provide a distinct selectivity advantage, reducing endogenous background, relative to use of lower m/z intense immonium ion fragments.

Another advantageous feature of the technology includes the use of a chromatography column including a chromatographic surface wherein the chromatographic surface includes a hydrophobic surface group and one or more ionizable modifiers, which can reduce secondary interactions and mimics the peak shape benefit for peptides that was historically achieved through the use of trifluoroacetic acid (TFA) in reversed-phase chromatography systems. Accordingly, the technology can obtain peak widths that are significantly narrower than traditional columns using formic acid in the mobile phase.

Yet another advantageous feature of the technology includes the synergistic effect of combining a highly selective sample preparation method (e.g., multi-step mixed-mode or reversed phase polymeric SPE), coupled to a high resolution chromatographic method (e.g., LC column chemistry wherein the chromatographic surface includes a hydrophobic surface group and one or more ionizable modifiers), and a high sensitivity MS platform (e.g., triple quadrupole MS, analyte-specific high m/z fragments) for analyzing polypeptides. As a result, the technology is highly selective (e.g., can resolve related compounds that ELISA and MS methods relying on smaller/immonium ions cannot) and highly sensitive (e.g., effective in small samples and low concentration solutions) for large molecules such as polypeptides.

In one aspect, the technology features a method for identifying and/or quantifying a polypeptide in a specimen. The method includes (i) treating a specimen suspected of including a polypeptide with a base, (ii) extracting a first fraction of the treated specimen by solid phase extraction using a mixed mode or polymeric reversed-phase media and a first solvent including an acid, (iii) separating a component of the first fraction by liquid chromatography using a chromatographic surface including a hydrophobic surface group, and one or more ionizable modifiers, and a second solvent including an acid, and (iv) analyzing the component of the first fraction by mass spectroscopy, thereby identifying and/or quantifying the polypeptide, if present, using a signal corresponding to a transition from a multiply charged precursor to a sequence fragment ion from the polypeptide.

In another aspect, the technology features a method for identifying an insulin in a specimen. The method includes (i) treating a specimen suspected of including an insulin with a base, (ii) extracting a first fraction of the treated specimen by solid phase extraction using a mixed mode or polymeric reversed-phase mode media and a first solvent including an acid, (iii) separating a component of the first fraction by liquid chromatography using a chromatographic surface including a hydrophobic surface group and one or more ionizable modifiers, and a second solvent including an acid, and (iv) analyzing the component of the first fraction by mass spectroscopy, thereby identifying the insulin, if present, using a signal corresponding to a transition from a multiply charged precursor to a sequence fragment ion from the insulin.

In yet another aspect, the technology features a method for quantifying an insulin (or other polypeptide) in a specimen. The method includes (i) treating a specimen suspected of including an insulin with 2-amino-2-hydroxymethyl-propane-1,3-diol, (ii) extracting a first fraction of the treated specimen by solid phase extraction using a mixed mode media operating in cation exchange and reverse phase modes and a first solvent including acetic acid, (iii) separating a component of the first fraction by liquid chromatography using a chromatographic surface including a hydrophobic surface group and one or more ionizable modifiers, and a second solvent including formic acid, and (iv) analyzing the component of the first fraction by triple quadrupole mass spectroscopy operated in positive electrospray ionization mode, thereby quantifying the insulin, if present, using a signal corresponding to an intact multiply charged precursor fragment selected in a first quadrupole and its corresponding sequence fragment ion selected in a final quadrupole.

In still yet another aspect, the technology features a method for assessing the bioequivalence of a first polypeptide and a second polypeptide. The method includes (i) obtaining a specimen from a bioequivalence assay for a first polypeptide, (ii) treating the specimen with a base, (iii) extracting a first fraction of the treated specimen by solid phase extraction using a mixed mode or polymeric reversed-phase media and a first solvent including an acid, (iv) separating a component of the first fraction by liquid chromatography using a chromatographic surface including a hydrophobic surface group and one or more ionizable modifiers, and a second solvent including an acid, (v) analyzing the component of the first fraction by mass spectroscopy, thereby quantifying the first polypeptide using a signal corresponding to a sequence fragment ion from the first polypeptide, and (vi) comparing the quantity of the first polypeptide to a quantity of the second polypeptide expected in a bioequivalence assay for a first polypeptide, thereby determining if the first polypeptide and second polypeptide are bioequivalent.

Any of the above aspects can be combined with any one or more of the embodiments listed below and/or any one or more features provided in the specification and drawings.

In various embodiments, a method can further include quantifying the amount of the insulin (or other polypeptide), if present, using the signal corresponding to the sequence fragment ion from the insulin, where the signal corresponds to an intact multiply charged precursor fragment selected in a first quadrupole and its corresponding sequence fragment ion selected in a final quadrupole, and where the sequence fragment ion exhibits an m/z>800. Where the method is used on another polypeptide, the sequence fragment ion can exhibit an m/z that is characteristic of that polypeptide in an undigested state.

In some embodiments, the base includes 2-amino-2-hydroxymethyl-propane-1,3-diol.

In certain embodiments, treating the specimen further includes an organic precipitation.

In various embodiments, the mixed mode media includes ion exchange moieties and reverse phase moieties. The ion exchange can include cation exchange.

In some embodiments, the first solvent includes acetic acid. The second solvent can include acetic acid and/or formic acid.

In certain embodiments, the component of the first fraction includes undigested insulin. Where the method is used on another polypeptide, the first fraction can include that polypeptide in an undigested state.

In various embodiments, the mass spectrometry includes triple quadrupole mass spectrometry. The mass spectrometry can be carried out in positive electrospray ionization mode.

In some embodiments, the sequence fragment ion exhibits an m/z>800. Where the method is used on another polypeptide, the sequence fragment ion can exhibit an m/z that is characteristic of that polypeptide in an undigested state.

In certain embodiments, the detection limit of the insulin (or polypeptide of interest) is 0.25 ng/mL or less. The detection limit of the polypeptide of interest can be 0.50 ng/mL or less. The detection limit can be achieved in a specimen of 250 microliters or less. In certain embodiments, the detection limit for a polypeptide of interest can be 30 pg/mL. In some embodiments, the detection limit for a polypeptide of interest can be 15 pg/mL.

In various embodiments, analyzing the component of the first fraction by mass spectroscopy can resolve any two or more of insulin glargine, insulin detemir, insulin aspart, insulin glulisine, or human insulin.

In some embodiments, the method further includes quantifying the amount of the insulin, if present, using the signal corresponding to the sequence fragment ion from the insulin.

In certain embodiments, the signal corresponds to an intact multiply charged precursor fragment selected in a first quadrupole and its corresponding sequence fragment ion selected in a final quadrupole.

In various embodiments, bioequivalence is determined based upon the absence of a significant difference in the rate and extent to which the first polypeptide (e.g., first insulin) and second polypeptide (e.g., second insulin) become available at the site of drug action when administered at the same molar dose under similar conditions in the bioequivalence assay.

In some embodiments, the bioequivalence assay includes a pharmacokinetic study.

In certain embodiments, the bioequivalence assay includes a pharmacodynamics study.

In various embodiments, the bioequivalence assay includes a clinical trial.

In some embodiments, the bioequivalence assay includes an in vitro test.

In certain embodiments, the first polypeptide and the second polypeptide are each independently insulin glargine, insulin detemir, insulin aspart, insulin glulisine, human insulin, or a derivative or analog thereof.

In various embodiments, the first polypeptide and the second polypeptide are each independently exenatide, hepcidin, teriparatide, enfuvirtide, calcitonin, brain natriuretic peptide (BNP), amyloid beta peptides, GLP-1, glucagon, bombesin, or a derivative or analog thereof.

In some embodiments, analyzing the component of the first fraction by mass spectroscopy can resolve any two or more of insulin glargine, insulin detemir, insulin aspart, insulin glulisine, human insulin, or a derivative or analog thereof.

In certain embodiments, analyzing the component of the first fraction by mass spectroscopy can resolve any two or more of exenatide, hepcidin, teriparatide, enfuvirtide, calcitonin, brain natriuretic peptide (BNP), amyloid beta peptides, GLP-1, glucagon, bombesin, or a derivative or analog thereof.

The present technology is described in further detail by the figures and examples below, which are used only for illustration purposes and are not limiting.

BRIEF DESCRIPTION OF THE DRAWINGS

FIGS. 4A-4C shows chromatograms for Lantus® (insulin glargine) at various concentrations.

FIGS. 5A-5C shows the linearity for Lantus® (insulin glargine) in solvent standards.

FIGS. 6A-6C shows chromatograms for Lantus® (insulin glargine) extracted from human plasma and analyzed in accordance with the technology.

FIGS. 7A-7E shows chromatograms for additional levels and integration for Lantus® (insulin glargine).

FIGS. 12A-12C shows chromatograms and peak integrations for Levemir® (insulin detemir) extracted from human plasma and analyzed in accordance with the technology.

FIGS. 14A-14C shows chromatograms for Apidra® (insulin glulisine) at various concentrations.

FIGS. 15A-15C shows the linearity for Apidra® (insulin glulisine) in solvent standards.

FIGS. 16A-16C shows chromatograms and peak integrations for Apidra® (insulin glulisine) extracted from human plasma and analyzed in accordance with the technology.

FIGS. 18E-18F shows an integrated analyte peak from the chromatograms shown in FIGS. 18A-18D.

FIGS. 21A-21B shows example chromatograms from final eluates from samples pretreated with TRIS.

FIGS. 21C-21D shows example chromatograms from final eluates from samples pretreated with TFA.

FIGS. 23A-23C show representative chromatograms of an extracted plasma blank and insulin glulisine at the LOD and LLOQ.

DETAILED DESCRIPTION OF THE TECHNOLOGY

Figure 1:
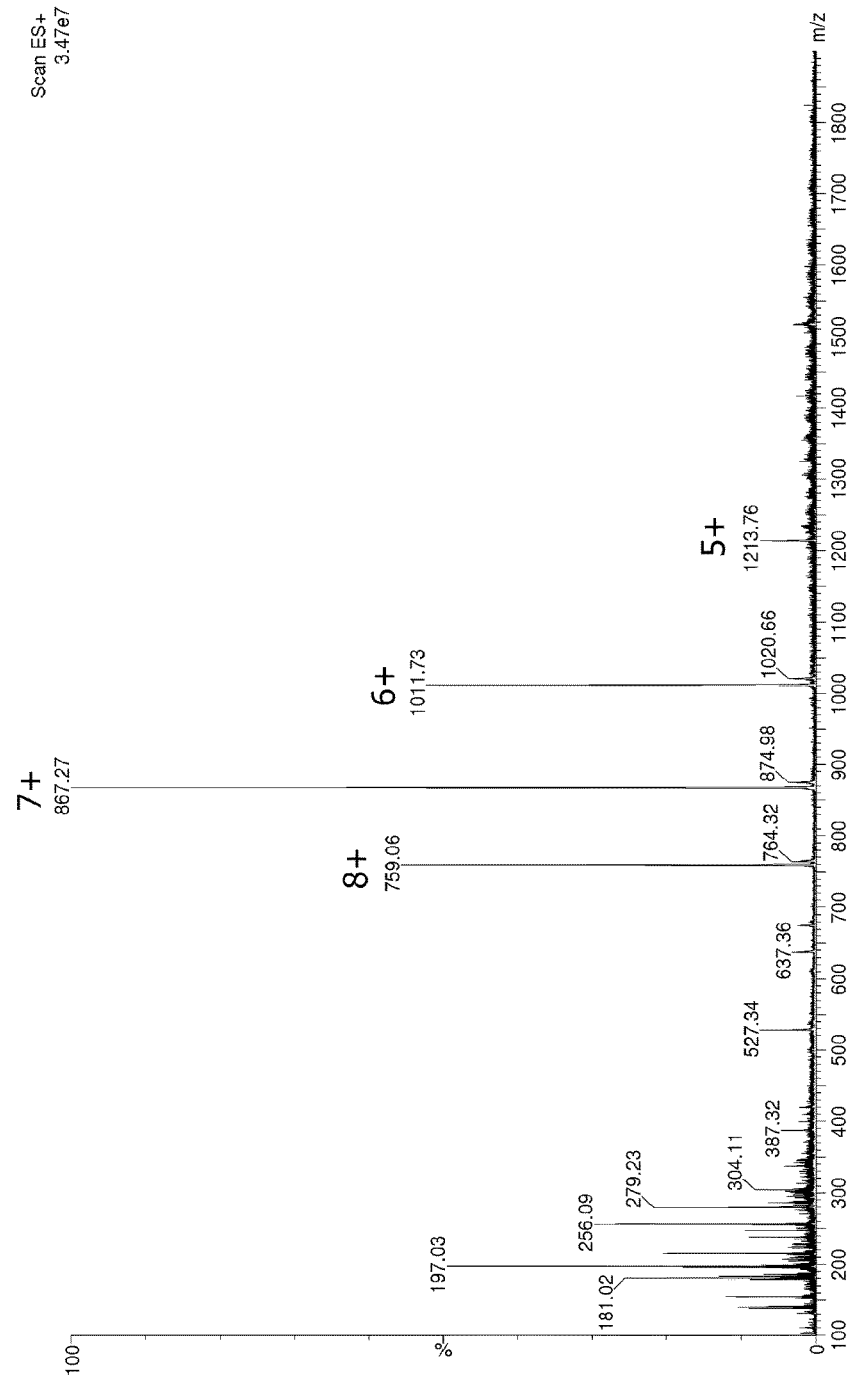
FIG. 1 shows a MS scan of Lantus® (insulin glargine).

The technology provides methods, as well as corresponding composition, kits, and apparatuses for quantifying a polypeptide analyte in a sample. The technology can employ combinations of mixed-mode or reversed phase solid phase extraction, liquid chromatography using a chromatographic surface including a hydrophobic surface group and one or more ionizable modifiers, (e.g., with columns having <2 micrometer particles), and high sensitivity mass spectroscopy for identification and quantification of polypeptides. MS can employ sequence fragment ions from the polypeptide, for example, intact multiply charged precursor fragments selected in a first quadrupole and corresponding sequence fragment ion selected in a final quadrupole, where the sequence fragment ion exhibits an m/z that is characteristic of that polypeptide in an undigested state. An example chromatographic surface including a hydrophobic surface group and one or more ionizable modifiers can be a charged surface hybrid column, for instance an ACQUITY UPLC® CSH or XSelect™ column, commercially available from Waters Technology Corp., Milford, Mass. The following detailed description provides additional description of the analytes and samples, followed by the pre-treatment, separation, and analysis steps and, finally, illustrative examples.

Analytes

Further to the summary above, analytes or target polypeptide analytes can include essentially any polypeptide of interest that can be detected using a mass spectrometer. The target analyte can be of interest, for example, in one or more of clinical chemistry, medicine, veterinary medicine, forensic chemistry, pharmacology, food industry, safety at work, and environmental pollution.

Clinical chemistry target analytes can include any polypeptide present in an organism (e.g., human body, animal body, fungi, bacterium, virus, and the like). For example, clinical chemistry target analytes include, but are not limited to, proteins, protein metabolites, protein biomarkers, and polypeptide drugs and their metabolites.

Human medicine and veterinary medicine target analytes can include any polypeptide that can be used for the diagnosis, prophylaxis or treatment of a disease or condition in a subject. For example, human medicine and veterinary medicine target analytes include, but are not limited to, disease markers, prophylactic, or therapeutic agents.

Forensic chemistry target analytes can include any polypeptide present in a sample taken from the site of crime, such as a sample from a victim's body (e.g., tissue or fluid sample, hair, blood, semen, urine, and the like). For example, clinical chemistry target analytes include, but are not limited to, toxic agents, drugs and their metabolites, biomarkers, and identifying compounds.

Pharmacology target analytes can include any polypeptide that is a pharmaceutical or metabolite thereof or which can be used for the design, synthesis, and monitoring of drugs. For example, pharmacology target analytes include, but are not limited to, polypeptide prophylactic and/or therapeutic agents, their prodrugs, intermediates and metabolites. Pharmacological analysis can include bioequivalence testing, for example, in connection with the approval, manufacturing, and monitoring of a generic drug.

Food industry and agricultural target analytes can include any polypeptide that is relevant for monitoring of the safety of foods, beverages, and/or other food industry/agricultural products. Examples of target analytes from the field of food industry include, but are not limited to, polypeptide pathogen markers, allergens (e.g., gluten and nut proteins), and mycotoxins.

Target analytes can include polypeptides (e.g., polymers of naturally and/or non-naturally occurring amino acids such as Gly, Ala, Val, Leu, Ile, Pro, Phe, Trp, Cys, Met, Ser, Thr, Tyr, His, Lys, Arg, Asp, Glu, Asn, Gln, selenocysteine, ornithine, citrulline, hydroxyproline, methyllysine, carboxyglutamate), peptides, polypeptides, proteins, glycoproteins, lipoproteins; peptide-nucleic acids; hormones (such as peptide hormones (e.g., TRH and vasopressin), as well as synthetic and industrial polypeptides.

In some embodiments, target analytes can include peptides and/or polypeptides that are difficult to identify and/or quantify by conventional methods (e.g., ligand binding assays such as ELISA). Such peptides or polypeptides can be difficult to identify and/or quantify because no antibody to the polypeptide of interest is available, and/or because it is difficult to distinguish the polypeptide analyte from a metabolite or analog thereof.

Furthermore, in some embodiments, target peptides or polypeptides can be difficult to analyze by conventional methods (e.g., ligand binding assays such as ELISA) because they exhibit a high degree of non-specific binding, they are greater than about 3,000 Daltons in molecular weight, they form aggregates, they fragment poorly in a mass spectrometer, they are highly polar (e.g., they require mixed-mode SPE approaches in order to efficiently bind and release them during sample preparation), they are highly non-polar (e.g., they require a high percentage of modifiers to release them from extraction media and keep them in solution), they need to be separated from isobaric peptides in the sample that are at much higher concentrations, they have poor transfer efficiency in and out of chromatographic pools of LC and SPE columns, they suffer from significant secondary interactions with chromatographic media resulting in poor peak shape and/or inability to elute in a highly resolved band, they are unstable, and/or they undergo chemical modification under extreme pH conditions.

In some embodiments, target analyte peptides or polypeptides can include one or more of exenatide, hepcidin, teriparatide, enfuvirtide, calcitonin, brain natriuretic peptide (BNP), amyloid beta peptides, e.g., GLP-1, glucagon, bombesin, and derivatives or analogs thereof, and the like. In some embodiments, the target analyte can include one or more insulin, and/or insulin analogs such as Lantus® (insulin glargine), Levemir® (insulin detemir), Novolog/NovoRapid® (insulin aspart), and Apidra® (insulin glulisine).

Samples

In general, a sample is a composition including at least one target analyte (e.g., an analyte of the class or kind disclosed above, together with a matrix). Samples can include a solid, liquid, gas, mixture, material (e.g., of intermediary consistency, such as an extract, cell, tissue, organisms) or a combination thereof. In various embodiments, the sample is a bodily sample, an environmental sample, a food sample, a synthetic sample, an extract (e.g., obtained by separation techniques), or a combination thereof.

Bodily samples can include any sample that is derived from the body of an individual. In this context, the individual can be an animal, for example a mammal, for example a human. Other example individuals include a mouse, rat, guinea-pig, rabbit, cat, dog, goat, sheep, pig, cow, or horse. The individual can be a patient, for example, an individual suffering from a disease or being suspected of suffering from a disease. A bodily sample can be a bodily fluid or tissue, for example taken for the purpose of a scientific or medical test, such as for studying or diagnosing a disease (e.g., by detecting and/or identifying a pathogen or the presence of a biomarker). Bodily samples can also include cells, for example, pathogens or cells of the individual bodily sample (e.g., tumor cells). Such bodily samples can be obtained by known methods including tissue biopsy (e.g., punch biopsy) and by taking blood, bronchial aspirate, sputum, urine, feces, or other body fluids. Exemplary bodily samples include humor, whole blood, plasma, serum, umbilical cord blood (in particular, blood obtained by percutaneous umbilical cord blood sampling (PUBS), cerebrospinal fluid (CSF), saliva, amniotic fluid, breast milk, secretion, ichor, urine, feces, meconium, skin, nail, hair, umbilicus, gastric contents, placenta, bone marrow, peripheral blood lymphocytes (PBL), and solid organ tissue extract.

Environmental samples can include any sample that is derived from the environment, such as the natural environment (e.g., seas, soils, air, and flora) or the manmade environment (e.g., canals, tunnels, buildings). Exemplary environmental samples include water (e.g., drinking water, river water, surface water, ground water, potable water, sewage, effluent, wastewater, or leachate), soil, air, sediment, biota (e.g., soil biota), flora, fauna (e.g., fish), and earth mass (e.g., excavated material).

Food samples can include any sample that is derived from food (including beverages). Such food samples can be used for various purposes including, for example, (1) to check whether a food is safe; (2) to check whether a food contained harmful contaminants at the time the food was eaten (retained samples) or whether a food does not contain harmful contaminants; (3) to check whether a food contains only permitted additives (e.g., regulatory compliance); (4) to check whether it contains the correct levels of mandatory ingredients (e.g., whether the declarations on the label of the food are correct); or (5) to analyze the amounts of nutrients contained in the food. Exemplary food samples include edible products of animal, vegetable or synthetic origin (e.g., milk, bread, eggs, or meat), meals, drinks, and parts thereof, such as retain samples. Food samples can also include fruits, vegetables, pulses, nuts, oil seeds, oil fruits, cereals, tea, coffee, herbal infusions, cocoa, hops, herbs, spices, sugar plants, meat, fat, kidney, liver, offal, milk, eggs, honey, fish, and beverages.

Synthetic samples can include any sample that is derived from an industrial process. The industrial process can be a biological industrial process (e.g., processes using biological material containing genetic information and capable of reproducing itself or being reproduced in a biological system, such as fermentation processes using transfected cells) or a non-biological industrial process (e.g., the chemical synthesis or degradation of a compound such as a pharmaceutical). Synthetic samples can be used to check and monitor the progress of the industrial process, to determine the yield of the desired product, and/or measure the amount of side products and/or starting materials.

Pre-Treatment

Further to the summary above, the technology includes (i) treating a specimen suspected of including a polypeptide with a base and (ii) extracting a first fraction of the treated specimen by solid phase extraction using a mixed mode or a polymeric reversed-phase media and a first solvent including an acid. The pre-treatment steps of the technology work in concert with the separation and analysis steps, to provide a high resolution tool for studying polypeptides. In various embodiments, the pre-treatment can be adapted to avoid, minimize, mitigate, or otherwise control the digestion of the polypeptide analyte and to impart further selectivity onto the final extract.

Treatment with a base can include mixing the sample with bases used in the art for pre-treatment (e.g., as opposed to prior art methods that call for dilution of the sample with an acid). For example, the treatment can use TRIS base (e.g., 2-amino-2-hydroxymethyl-propane-1,3-diol). Treatment with base can be carried out prior to loading the sample for extraction. Treatment with base can eliminate potentially interfering polypeptides such as serum albumin from the sample, thereby improving the quality of the analysis.

Extracting a first fraction of the treated specimen by solid phase extraction (SPE) can include using a mixed mode or a polymeric reversed-phase media and a first solvent including an acid. In various embodiments, the mixed mode media includes ion exchange moieties and reverse phase moieties. The ion exchange can include cation exchange. An example SPE media is a Waters Oasis® HLB μElution 96-well plate.

Accordingly, the extraction (e.g., in combination with the separation) imparts orthogonality into the methods of the technology, by separating on the basis of different physical properties (e.g., both charge and hydrophobicity).

In various embodiments, elution solvents (e.g., in pre-treatment and/or separation) include an acid. An example solvent is acetic acid in water/organic. The acid in the solvent can facilitate solubilization of the polypeptide analyte and mitigate adsobtion of the polypeptide analyte during processing. The use of acid allows for the minimization or elimination of organic solvents, which can cause polypeptide precipitation.

In certain embodiments, the technology can include one or more additional pre-treatment steps or techniques. For example, treating the specimen can also include an organic precipitation.

In certain embodiments, dilution with TRIS base at pH 9-9.5 instead of dilution with an acid significantly improved recovery and reduced endogenous background. For instance, FIGS. 21A and 21C shows chromatograms from the final eluates from samples pretreated with TFA contained a broad, intense interference peak at 5.76 minutes that was absent from eluates pretreated with TRIS. These samples were further analyzed using full scan MS to elucidate the nature of the peak. Spectra were summed from 5.5 to 6.25 minutes samples from both pre-treatments, and the resultant data are shown in the bottom panels of FIGS. 21B and 21D. Deconvolution of the protein envelope in the samples pretreated with TFA produced an intact MW of approximately 66,400, providing putative identification as human serum albumin (HSA). HSA is typically present at approximately 35-50 mg/mL and must be efficiently removed and separated from the insulin analytes. Pretreatment with TRIS efficiently achieved this goal, as evidenced by the absence of the large protein peak at 5.66 minutes.

Separation

Further to the summary above, the technology includes separating a component of the first fraction by liquid chromatography using a chromatographic surface including a hydrophobic group surface and one or more ionizable modifiers, and a second solvent including an acid. The separation step of the technology works in concert with the pre-treatment and analysis steps, to provide a high resolution tool for studying polypeptides. In various embodiments, the separation can be adapted to avoid, minimize, mitigate, or otherwise control the digestion of the polypeptide analyte.

The chromatography columns of the technology can include a chromatographic surface having a hydrophobic surface group and one or more ionizable modifiers, and can facilitate separations by minimizing secondary interactions (e.g., due to + charges on the stationary phase surface). The chromatography columns can also allow for the use of formic acid in the mobile phase (e.g., in contrast to the TFA in the mobile phase). Accordingly, the technology provides for narrow peaks (e.g., 2-4× narrower than conventional chromatography setups), which improves signal to noise ratios and detection limits (e.g., especially for analytes at low concentration). One example chromatographic surface including a hydrophobic surface group and one or more ionizable modifiers is a Waters ACQUITY CSH™ C18 2.1×50 mm, 1.7 μm column. The second solvent can include formic acid (e.g., 0.1-1% formic acid in water).

In some embodiments, addition of a carrier protein can be an effective way to minimize nonspecific binding (NSB). For instance, for simplicity, 0.05% rat plasma can be added to the sample diluents, resulting in improved linearity in solvent standards. NSB can also occur between peptide analytes and the chromatographic columns LC columns may have to be "pretreated" by injection of protein precipitated plasma in order to obtain the best performance for biomolecules such as insulin. The plasma components presumably coat the column surface and effectively minimize NSB. In certain embodiments, these changes can result in reproducible peak areas and a broad linear dynamic range in solvent standards as well as an easily achievable LLOQ of 50 pg/mL for solvent standards.

Chromatographic Surface Materials

Chromatographic surface materials for use with the instant invention can include high purity chromatographic materials (HPCMs). For example, a chromatographic surface can incluse a hydrophobic surface group and one or more ionizable modifiers. Chromatographic surfaces can be used, for example, in chromatographic columns. In some embodiments, the ionizable modifier does not contain a Zwitterion, the ionizable modifier does not contain a quaternary ammonium ion moiety.

The term "high purity" or "high purity chromatographic material" can include a material which is prepared from high purity precursors. In certain aspects, high purity materials have reduced metal contamination and/or non-diminished chromatographic properties including, but not limited to, the acidity of surface silanols and the heterogeneity of the surface.

The term "chromatographic surface" can include a surface which provides for chromatographic separation of a sample. In certain aspects, the chromatographic surface is porous. In some aspects, a chromatographic surface may be the surface of a particle, a superficially porous material or a monolith. In certain aspects, the chromatographic surface is composed of the surface of one or more particles, superficially porous materials or monoliths used in combination during a chromatographic separation. In certain other aspects, the chromatographic surface is non-porous.

The term "ionizable modifier" can include a functional group which bears an electron donating or electron withdrawing group. In certain aspects, the ionizable modifier contains one or more carboxylic acid groups, amino groups, imido groups, amido groups, pyridyl groups, imidazolyl groups, ureido groups, thionyl-ureido groups or aminosilane groups, or a combination thereof. In other aspects, the ionizable modifier contains a group bearing a nitrogen or phosphorous atom having a free electron lone pair. In certain aspects, the ionizable modifier is covalently attached to the material surface and has an ionizable group. In some instances it is a attached to the chromatographic material by chemical modification of a surface hybrid group.

The term "hybrid", including "hybrid inorganic/organic material," can include inorganic-based structures wherein an organic functionality is integral to both the internal or "skeletal" inorganic structure as well as the hybrid material surface. The inorganic portion of the hybrid material may be, e.g., alumina, silica, titanium, cerium, or zirconium or oxides thereof, or ceramic material. "Hybrid" includes inorganic-based structures wherein an organic functionality is integral to both the internal or "skeletal" inorganic structure as well as the hybrid material surface. As noted above, exemplary hybrid materials are shown in U.S. Pat. Nos. 4,017,528, 6,528,167, 6,686,035 and 7,175,913.

The term "hydrophobic surface group" can include a surface group on the chromatographic surface which exhibits hydrophobicity. In certain aspects, a hydrophobic group can be a carbon bonded phase such as a C4 to C18 bonded phase. In other aspects, a hydrophobic surface group can contain an embedded polar group such that the external portion of the hydrophobic surface maintains hydrophobicity. In some instances it is a attached to the chromatographic material by chemical modification of a surface hybrid group. In other instances the hydrophobic group can be C4-C30, embedded polar, chiral, phenylalkyl, or pentafluorophenyl bonding and coatings.

In certain aspects the HPCM may further comprise a chromatographic core material. In some aspects, the chromatographic core is a silica material; a hybrid inorganic/organic material; a superficially porous material; or a superficially porous particle. The chromatographic core material may be in the form of discreet particles or may be a monolith. The chromatographic core material may be any porous material and may be commercially available or may be produced by known methods, such as those methods described in, for example, in U.S. Pat. Nos. 4,017,528, 6,528,167, 6,686,035 and 7,175,913. In some embodiments, the chromatographic core material may be a non-porous core.

The term "monolith" is intended to include a collection of individual particles packed into a bed formation, in which the shape and morphology of the individual particles are maintained. The particles are advantageously packed using a material that binds the particles together. Any number of binding materials that are well known in the art can be used such as, for example, linear or cross-linked polymers of divinylbenzene, methacrylate, urethanes, alkenes, alkynes, amines, amides, isocyanates, or epoxy groups, as well as condensation reactions of organoalkoxysilanes, tetraalkoxysilanes, polyorganoalkoxysiloxanes, polyethoxysiloxanes, and ceramic precursors. In certain embodiments, the term "monolith" also includes hybrid monoliths made by other methods, such as hybrid monoliths detailed in U.S. Pat. No. 7,250,214; hybrid monoliths prepared from the condensation of one or more monomers that contain 0-99 mole percent silica (e.g., $SiO_2$); hybrid monoliths prepared from coalesced porous inorganic/organic particles; hybrid monoliths that have a chromatographically-enhancing pore geometry; hybrid monoliths that do not have a chromatographically-enhancing pore geometry; hybrid monoliths that have ordered pore structure; hybrid monoliths that have non-periodic pore structure; hybrid monoliths that have non-crystalline or amorphous molecular ordering; hybrid monoliths that have crystalline domains or regions; hybrid monoliths with a variety of different macropore and mesopore properties; and hybrid monoliths in a variety of different aspect ratios. In certain embodiments, the term "monolith" also includes inorganic monoliths, such as those described in G. Guiochon/*J. Chromatogr. A* 1168 (2007) 101-168.

The term "chromatographic core" can include chromatographic materials, including but not limited to an organic material such as silica or a hybrid material, as defined herein, in the form of a particle, a monolith or another suitable structure which forms an internal portion of the materials of the invention. In certain aspects, the surface of the chromatographic core represents the chromatographic surface, as defined herein, or represents a material encased by a chromatographic surface, as defined herein. The chromatographic surface material may be disposed on or bonded to or annealed to the chromatographic core in such a way that a discrete or distinct transition is discernible or may be bound to the chromatographic core in such a way as to blend with the surface of the chromatographic core resulting in a gradation of materials and no discrete internal core surface. In certain embodiments, the chromatographic surface material may be the same or different from the material of the chromatographic core and may exhibit different physical or physiochemical properties from the chromatographic core, including, but not limited to, pore volume, surface area, average pore diameter, carbon content or hydrolytic pH stability.

The composition of the chromatographic surface material and the chromatographic core material (if present) may be varied by one of ordinary skill in the art to provide enhanced chromatographic selectivity, enhanced column chemical stability, enhanced column efficiency, and/or enhanced mechanical strength. Similarly, the composition of the surrounding material provides a change in hydrophilic/lipophilic balance (HLB), surface charge (e.g., isoelectric point or silanol pKa), and/or surface functionality for enhanced chromatographic separation. Furthermore, in some embodiments, the composition of the chromatographic material may also provide a surface functionality for available for further surface modification.

The ionizable modifiers and the hydrophobic surface groups of the HPCMs of the invention can be prepared using known methods. Some of the ionizable modifier reagents are commercially available. For example silanes having amino alkyl trialkoxysilanes, methyl amino alkyl trialkoxysilanes, and pyridyl alkyl trialkoxysilanes are commercially available. Other silanes such as chloropropyl alkyl trichlorosilane and chloropropyl alkyl trialkoxysilane are also commercially available. These can be bonded and reacted with imidazole to create imidazolyl alkyl silyl surface species, or bonded and reacted with pyridine to create pyridyl alkyl silyl surface species. Other acidic modifiers are also commercially available, including, but not limited to, sulfopropyl-trisilanol, carboxyethylsilanetriol, 2-(carbomethoxy)ethylmethyldichlorosilane, 2-(carbomethoxy)ethyltrichlorosilane, 2-(carbomethoxy)ethyltrimethoxysilane, n-(trimethoxysilylpropyl)ethylenediamine, triacetic acid, (2-diethylphosphato-ethyl)triethoxysilane, 2-(chlorosulfonylphenyl)ethyltrichlorosilane, and 2-(chlorosulfonylphenyl)ethyltrimethoxysilane.

It is known to one skilled in the art to synthesize these types of silanes using common synthetic protocols, including grinard reactions and hydrosilylations. Products can be purified by chromatography, recrystallization or distillation.

Other additives such as isocyanates are also commercially available or can be synthesized by one skilled in the art. A common isocyanate forming protocol is the reaction of a primary amine with phosgene or a reagent known as Triphosgene.

The ionizable modifier can contain a carboxylic acid group, a sulfonic acid group, a phosphoric acid group, a boronic acid group, an amino group, an imido group, an amido group, a pyridyl group, an imidazolyl group, an ureido group, a thionyl-ureido group or an aminosilane group.

In other aspects the ionizable modifier reagent may be selected from groups formula (I)

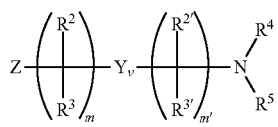

(I)

the formula (II)

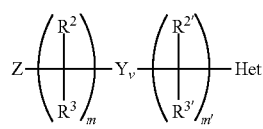

(II)

the formula (III)

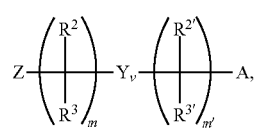

(III)

wherein m is an integer from 1-8;
v is 0 or 1;
when v is 0, m' is 0;
when v is 1, m' is an integer from 1-8;
Z represents a chemically reactive group, including (but not limited to)

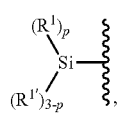

—OH, —OR$^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl or —I;

Y is an embedded polar functionality;

each occurrence of R$^1$ independently represents a chemically reactive group on silicon, including (but not limited to) —H, —OH, —OR$^6$, dialkylamine, triflate, Br, Cl, I, vinyl, alkene, or —(CH$_2$)$_{m''}$Q;

each occurrence of Q is —OH, —OR$^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I;

m" is an integer from 1-8;

p is an integer from 1-3;

each occurrence of R$^{1'}$ independently represents F, C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl, fluoroalkyl, or fluoroaryl;

each occurrence of R$^2$, R$^{2'}$, R$^3$ and R$^{3'}$ independently represents hydrogen, C$_1$-C$_{18}$ alkyl, C$_2$-C$_{18}$ alkenyl, C$_2$-C$_{18}$ alkynyl, C$_3$-C$_{18}$ cycloalkyl, C$_2$-C$_{18}$ heterocycloalkyl, C$_5$-C$_{18}$ aryl, C$_5$-C$_{18}$ aryloxy, or C$_1$-C$_{18}$ heteroaryl, —Z, or a group having the formula —Si(R')$_b$R"$_a$ or —C(R')$_b$R"$_a$;

a and b each represents an integer from 0 to 3 provided that a+b=3;

R' represents a C$_1$-C$_6$ straight, cyclic or branched alkyl group;

R" is a functionalizing group selected from the group consisting of alkyl, alkenyl, alkynyl, aryl, cyano, amino, diol, nitro, ester, a cation or anion exchange group, an alkyl or aryl group containing an embedded polar functionality and a chiral moiety.

R$^4$ represents hydrogen, C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl;

R$^5$ represents hydrogen, C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl;

each occurrence of R$^6$ independently represents C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl;

Het represents a heterocyclic or heteroaryl ring system comprising at least one nitrogen atom; and A represents an acidic ionizable modifier moiety or a dual charge ionizable modifier moiety.

In certain aspects, where the ionizable modifying reagent is selected from formulas (I), (II) or (III), m is 2 or 3.

In some aspects, where the ionizable modifying reagent is selected from formulas (I), (II) or (III), R$^1$ represents Cl, —OH, dialkylamino, methoxy or ethoxy.

In certain aspects, where the ionizable modifying reagent is selected from formulas (I), (II) or (III), R$^{1'}$ represents, methyl, ethyl, isobutyl, isopropyl or tert-butyl.

In other aspects where the ionizable modifying reagent is selected from formulas (I), (II) or (III), each occurrence of R$^2$ and R$^3$ represents hydrogen.

In other aspects where the ionizable modifying reagent is selected from formulas (I), (II) or (III), each occurrence of R$^{2'}$ and R$^{3'}$ represents hydrogen.

In other aspects where the ionizable modifying reagent is selected from formula each of R$^4$ and R$^5$ represents hydrogen.

In still other aspects where the ionizable modifying reagent is selected from formulas (II), Het is pyridyl, pyrimidinyl, pyridazinyl, pyrazinyl, piperidinyl, piperizinyl, hexahydropyrimidinyl, pyrrolyl, pyrazolyl, imidazolyl, pyrrolidinyl, pyrazolidinyl, imidazolidinyl or triazinyl.

In other aspects where the ionizable modifying reagent is selected from formulas (I), (II) or V is 1, m' is 3, and each occurrence of $R^2$, $R^{2'}$, $R^3$ and $R^{3'}$ is hydrogen. In certain aspects, where the ionizable modifying reagent is selected from formulas (I), (II) or (III), V is 1, m' is 3, and each occurrence of $R^2$, $R^{2'}$, $R^3$ and $R^{3'}$ is hydrogen, Y is carbamate, carbonate, amide, urea, ether, thioether, sulfinyl, sulfoxide, sulfonyl, thiourea, thiocarbonate, thiocarbamate or triazole.

In yet other embodiments, the ionizable modifier is aminopropyltriethoxysilane, aminopropyltrimethoxysilane, 2-(2-(trichlorosilyl)ethyl)pyridine, 2-(2-(trimethoxy)ethyl) pyridine, 2-(2-(triethoxy)ethyl)pyridine, 2-(4-pyridylethyl) triethoxysilane, 2-(4-pyridylethyl)trimethoxysilane, 2-(4-pyridylethyl)trichlorosilane, chloropropyltrimethoxysilane, chloropropyltrichlorosilane, chloropropyltrichlorosilane, chloropropyltriethoxysilane, imidazolylpropyltrimethoxysilane, imidazolylpropyltriethoxysilane, imidazolylpropyl trichlorosilane, sulfopropyltrisilanol, carboxyethylsilanetriol, 2-(carbomethoxy)ethylmethyldichlorosilane, 2-(carbomethoxy)ethyltrichlorosilane, 2-(carbomethoxy)ethyltrimethoxysilane, n-(trimethoxysilylpropyl)ethylenediamine triacetic acid, (2-diethylphosphatoethyl)triethoxysilane, 3-mercaptopropyltriethoxysilane, 3-mercaptopropyltrimethoxysilane, bis[3-(triethoxysilyl)propyl]disulfide, bis[3-(triethoxysilyl)propyl]tetrasulfide, 2,2-dimethoxy-1-thia-2-silacyclopentane, bis(trichlorosilylethyl)phenylsulfonyl chloride, 2-(chlorosulfonylphenyl)ethyltrichlorosilane, 2-(chlorosulfonylphenyl)ethyltrimethoxysilane, 2-(ethoxysulfonylphenyl)ethyltrimethoxysilane, 2-(ethoxysulfonylphenyl)ethyltrimethoxysilane, 2-(ethoxysulfonylphenyl)ethyltrichlorosilane, sulphonic acid phenethyltrisilanol, (triethoxysilyl ethyl)phenyl phosphonic acid diethyl ester, (trimethoxysilyl ethyl)phenyl phosphonic acid diethyl ester, (trichlorosilyl ethyl)phenyl phosphonic acid diethyl ester, phosphonic acid phenethyltrisilanol, N-(3-trimethoxysilylpropyl)pyrrole, N-(3-triethoxysilylpropyl)-4,5-dihydroimidazole, bis(methyldimethoxysilylpropyl)-N-methylamine, tris(triethoxysilylpropyl)amine, bis(3-trimethoxysilylpropyl)-N-methylamine, (N,N-diethyl-3-aminopropyl) trimethoxysilane, N-(hydroxyethyl)-N-methylaminopropyltrimethoxysilane, 3-(N,N-dimethylaminopropyl) trimethoxysilane, bis(2-hydroxyethyl)-3-aminopropyltriethoxysilane, N,N'-bis(hydroxyethyl)-N,N'-bis(trimethoxysilylpropyl)ethylenediamine, or N,N-dimethyl-3-aminopropylmethyldimethoxysilane.

In certain embodiments, when the ionizable modifier is of the formula (II), the acidic ionizable modifiers is a protected or deprotected forms of trisilanol, trialkoxysilane or trichlorosilane; or a salt of sulfonic acid alkyl silanes, sulfonic acid phenylalkyl silanes, sulfonic acid benzylalkyl silanes, sulfonic acid phenyl silanes, sulfonic acid benzyl silanes, carboxylic acid alkyl silanes, carboxylic acid phenylalkyl silanes, carboxylic acid benzylalkyl silanes, carboxylic acid phenyl silanes, carboxylic acid benzyl silanes, phosphoric acid alkyl silanes, phosphonic acid phenylalkyl silanes, phosphonic acid benzylalkyl silanes, phosphonic acid phenyl silanes, phosphonic acid benzyl silanes, boronic acid alkyl silanes, boronic acid phenylalkyl silanes, boronic acid benzylalkyl silanes, boronic acid phenyl silanes, boronic acid benzyl silanes.

In certain embodiments, when the ionizable modifier is of the formula (III), the acidic ionizable modifiers is a protected or deprotected version or a salt of sulfonic acid alkyl isocyanates, sulfonic acid phenylalkyl isocyanates, sulfonic acid benzylalkyl isocyanates, sulfonic acid phenyl isocyanates, sulfonic acid benzyl isocyanates carboxylic acid alkyl isocyanates, carboxylic acid phenylalkyl isocyanates, carboxylic acid benzylalkyl isocyanates, carboxylic acid phenyl isocyanates, carboxylic acid benzyl isocyanates, phosphoric acid alkyl isocyanates, phosphonic acid phenylalkyl isocyanates, phosphonic acid benzylalkyl isocyanates, phosphonic acid phenyl isocyanates, phosphonic acid benzyl isocyanates, boronic acid alkyl isocyanates, boronic acid phenylalkyl isocyanates, boronic acid benzylalkyl isocyanates, boronic acid phenyl isocyanates, or boronic acid benzyl isocyanates.

In certain embodiments, when the ionizable modifier reagent is selected from formula (III), A represents a dual charge ionizable modifier moiety. While not limited to theory; the dual charge ionizable modifier moiety has two sub-groups that can display opposite charges. Under some conditions the dual charge ionizable modifier moiety can act similarly to a zwitterions and ampholytes to display both a positive and negative charge and maintain a zero net charge. Under other conditions the dual charge ionizable modifier moiety may only have one group ionized and may display a net positive or negative charge. Dual charge ionizable modifier moieties include, but are not limited to, alkyl, branched alkyl, aryl, cyclic, polyaromatic, polycyclic, hetrocyclic and polyheterocyclic groups that can display a positive charge (commonly on a nitrogen or oxygen atom), and a negative charge through an acidic group that includes a carboxylic, sulfonic, phosphonic or boronic acid. Alternatively, some metal containing complexes can display both positive and negative charges. Dual charge ionizable modifier moieties may also include, but are not limited to zwitterions, ampholyte, amino acid, aminoalkyl sulfonic acid, aminoalkyl carboxylic acid, mono and di-methylaminoalkyl sulfonic acid, mono and di-methylaminoalkyl carboxylic acid, pyridinium alkyl sulfonic acid, and pyridinium alkyl carboxylic acid groups. Alternatively the dual charge ionizable modifier moiety may be 2-(N-morpholino)ethanesulfonic acid, 3-(N-morpholino)propanesulfonic acid, 4-(2-hydroxyethyl)-1-piperazine ethanesulfonic acid), piperazine-N,N'-bis(2-ethanesulfonic acid), N-cyclohexyl-3-aminopropanesulfonic acid, N-cyclohexyl-2-hydroxyl-3-aminopropanesulfonic acid, 3-[(3-cholamidopropyl)dimethylammonio]-1-propanesulfonate, 6-Methyl-9,10-didehydro-ergoline-8-carboxylic acid, phenolsulfonphthalein, betaines, quinonoids, N,N-bis (2-hydroxyethyl)glycine, and N-[tris(hydroxymethyl) methyl]glycine groups.

The term "alkyl" includes saturated aliphatic groups, including straight-chain alkyl groups, branched-chain alkyl groups, cycloalkyl (alicyclic) groups, alkyl substituted cycloalkyl groups and cycloalkyl substituted alkyl groups. In certain embodiments, a straight chain or branched chain alkyl has 30 or fewer carbon atoms in its backbone, e.g., C1-C30 for straight chain or C3-C30 for branched chain. In certain embodiments, a straight chain or branched chain alkyl has 20 or fewer carbon atoms in its backbone, e.g., C1-C20 for straight chain or C3-C20 for branched chain, and more preferably 18 or fewer. Likewise, preferred cycloalkyls have from 4-10 carbon atoms in their ring structure and more preferably have 4-7 carbon atoms in the ring structure. The term "lower alkyl" refers to alkyl groups having from 1 to 6 carbons in the chain and to cycloalkyls having from 3 to 6 carbons in the ring structure.

Moreover, the term "alkyl" (including "lower alkyl") as used throughout the specification and claims includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl, e.g., having 1 to 3 separate or fused rings and from 6 to about 18 carbon ring atoms, e.g., phenylmethyl(benzyl).

The term "amino," as used herein, refers to an unsubstituted or substituted moiety of the formula —NRaRb, in which Ra and Rb are each independently hydrogen, alkyl, aryl, or heterocyclyl, or Ra and Rb, taken together with the nitrogen atom to which they are attached, form a cyclic moiety having from 3 to 8 atoms in the ring. Thus, the term "amino" includes cyclic amino moieties such as piperidinyl or pyrrolidinyl groups, unless otherwise stated. An "amino-substituted amino group" refers to an amino group in which at least one of Ra and Rb, is further substituted with an amino group.

The term "aromatic group" includes unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

The term "aryl" includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine and the like. Aryl groups also include polycyclic fused aromatic groups such as naphthyl, quinolyl, indolyl and the like. The aromatic ring can be substituted at one or more ring positions with such substituents, e.g., as described above for alkyl groups. Suitable aryl groups include unsubstituted and substituted phenyl groups. The term "aryloxy" as used herein means an aryl group, as defined above, having an oxygen atom attached thereto. The term "aralkoxy" as used herein means an aralkyl group, as defined above, having an oxygen atom attached thereto. Suitable aralkoxy groups have 1 to 3 separate or fused rings and from 6 to about 18 carbon ring atoms, e.g., O-benzyl.

The term "chiral moiety" is intended to include any functionality that allows for chiral or stereoselective syntheses. Chiral moieties include, but are not limited to, substituent groups having at least one chiral center, natural and unnatural amino-acids, peptides and proteins, derivatized cellulose, macrocyclic antibiotics, cyclodextrins, crown ethers, and metal complexes.

The term "embedded polar functionality" is a functionality that provides an integral polar moiety such that the interaction with basic samples due to shielding of the unreacted silanol groups on the silica surface is reduced. Embedded polar functionalities include, but are not limited to carbonate, amide, urea, ether, thioether, sulfinyl, sulfoxide, sulfonyl, thiourea, thiocarbonate, thiocarbamate, ethylene glycol, heterocyclic, triazole functionalities or carbamate functionalities such as disclosed in U.S. Pat. No. 5,374,755, and chiral moieties.

The term "heterocyclic group" includes closed ring structures in which one or more of the atoms in the ring is an element other than carbon, for example, nitrogen, sulfur, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like. Suitable heteroaromatic and heteroalicyclic groups generally will have 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

In some aspects, the ratio of the hydrophobic surface group:ionizable modifier in the HPCM of the invention is from about 2.5:1 to about 350:1; from about 3:1 to about 200:1; from about 4:1 to about 150:1; from about 4:1 to about 35:1; from about 5:1 to about 25:1; from about 5:1 to about 22:1; from about 20:1 to about 100:1; or from about 25:1 to about 100:1.

In some embodiments, the ratio of the hydrophobic surface group:ionizable modifier in the HPCM of the invention is from about 4:1 to about 150:1; from about 20:1 to about 100:1; or from about 25:1 to about 100:1.

In other aspects, the concentration of ionizable modifier in the HPCM of the invention is less than about 0.5 $\mu mol/m^2$; less than about 0.4 $\mu mol/m^2$; less than about 0.3 $\mu mol/m^2$; from about 0.01 $\mu mol/m^2$ to about 0.5 $\mu mol/m^2$; from about 0.01 $\mu mol/m^2$ to about 0.4 $\mu mol/m^2$; or from about 0.03 $\mu mol/m^2$ to about 0.3 $\mu mol/m^2$.

In other embodiments, the concentration of ionizable modifier in the HPCM of the invention is less than about 0.5 $\mu mol/m^2$; less than about 0.4 $\mu mol/m^2$; less than about 0.3 $mmol/m^2$; from about 0.01 $\mu mol/m^2$ to about 0.5 $\mu mol/m^2$; from about 0.1 $\mu mol/m^2$ to about 0.4 $\mu mol/m^2$; or from about 0.2 $\mu mol/m^2$ to about 0.3 $\mu mol/m^2$.

In another aspect, the hydrophobic surface group of the HPCM of the invention is a $C_4$ to $C_{30}$ bonded phase. In certain aspects, the hydrophobic surface group is a $C_1$ bonded phase. In other aspects, the hydrophobic surface group is an aromatic, phenylalkyl, fluoro-aromatic, phenylhexyl, pentafluorophenylalkyl or chiral bonded phase. In still other aspects, the hydrophobic surface group is an embedded polar bonded phase.

In certain aspects, the HPCM of the invention may be in the form of a particle, a granular material, a monolith, a superficially porous material, a superficially porous particle, a superficially porous monolith, or a superficially porous layer for open tubular chromatography.

In certain aspects, the HPCM of the invention may be in inorganic material (e.g., silica, alumina, titania, zirconia), a hybrid organic/inorganic material, an inorganic material (e.g., silica, alumina, titania, zirconia) with a hybrid surface layer, a hybrid material with an inorganic (e.g., silica, alumina, titania, zirconia) surface layer, or a hybrid material with a different hybrid surface layer. In other aspects, the HPCM of the invention may have ordered pore structure, non-periodic pore structuring, non-crystalline or amorphous pore structuring or substantially disordered pore structuring.

The term "substantially disordered" refers to a lack of pore ordering based on x-ray powder diffraction analysis. Specifically, "substantially disordered" is defined by the lack of a peak at a diffraction angle that corresponds to a d value (or d-spacing) of at least 1 nm in an x-ray diffraction pattern.

In still another aspect, the HPCM of the invention has a quantified surface coverage ratio, B/A, from about 2.5 to about 300 wherein A represents the ionizable modifier and B represents the hydrophobic group. In certain aspects, the quantified surface coverage ratio, B/A, is from about 3 to about 200, from about 4 to about 35 or from about 5 to about 22.

In another aspect, the hydrophobic surface group of the HPCM of the invention is a C4 to C18 bonded phase. In certain aspects, the hydrophobic surface group is a C18 bonded phase. In still other aspects, the hydrophobic surface group is an embedded polar bonded phase. In other aspects, the hydrophobic surface group is an aromatic, phenylalkyl, fluoro-aromatic, phenylhexyl, or pentafluorophenylalkyl bonded phase. In another aspect, the hydrophobic surface group is a $C_4$-$C_{30}$, embedded polar, chiral, phenylalkyl, or pentafluorophenyl bonding or coating.

In certain embodiments, the HPCM of the invention may be in the form of a particle, a monolith or a superficially porous material. In certain other aspects, the HPCM of the invention is a non-porous material.

In certain aspects, the HPCM of the invention may be an inorganic material (e.g., silica), a hybrid organic/inorganic material, an inorganic material (e.g., silica) with a hybrid surface layer, a hybrid particle with a inorganic (e.g., silica) surface layer, or a hybrid particle with a different hybrid surface layer.

In one embodiment, the HPCM of the invention does not have chromatographically enhancing pore geometry. In another embodiment, the HPCM of the invention has chromatographically enhancing pore geometry.

The language "chromatographically-enhancing pore geometry" includes the geometry of the pore configuration of the presently-disclosed materials, which has been found to enhance the chromatographic separation ability of the material, e.g., as distinguished from other chromatographic media in the art. For example, a geometry can be formed, selected or constructed, and various properties and/or factors can be used to determine whether the chromatographic separations ability of the material has been "enhanced", e.g., as compared to a geometry known or conventionally used in the art. Examples of these factors include high separation efficiency, longer column life and high mass transfer properties (as evidenced by, e.g., reduced band spreading and good peak shape.) These properties can be measured or observed using art-recognized techniques. For example, the chromatographically-enhancing pore geometry of the present porous inorganic/organic hybrid materials is distinguished from the prior art materials by the absence of "ink bottle" or "shell shaped" pore geometry or morphology, both of which are undesirable because they, e.g., reduce mass transfer rates, leading to lower efficiencies.

Chromatographically-enhancing pore geometry is found in hybrid materials containing only a small population of micropores. A small population of micropores is achieved in hybrid materials when all pores of a diameter of about <34 Å contribute less than about 110 $m^2$/g to the specific surface area of the material. Hybrid materials with such a low micropore surface area (MSA) give chromatographic enhancements including high separation efficiency and good mass transfer properties (as evidenced by, e.g., reduced band spreading and good peak shape). Micropore surface area (MSA) is defined as the surface area in pores with diameters less than or equal to 34 Å, determined by multipoint nitrogen sorption analysis from the adsorption leg of the isotherm using the BJH method. As used herein, the acronyms "MSA" and "MPA" are used interchangeably to denote "micropore surface area".

The term "functionalizing group" includes organic functional groups which impart a certain chromatographic functionality to a chromatographic stationary phase.

In certain embodiments, the HPCM of the invention has a surface area of about 25 to 1100 $m^2$/g; about 80 to 500 $m^2$/g; or about 120 to 330 $m^2$/g.

In other embodiments, the HPCM of the invention a pore volume of about 0.15 to 1.7 $cm^3$/g; or about 0.5 to 1.3 $cm^3$/g.

In certain other embodiments, the HPCM of the invention is non-porous.

In yet other embodiments, the HPCM of the invention has a micropore surface area of less than about 110 $m^2$/g; less than about 105 $m^2$/g; less than about 80 $m^2$/g; or less than about 50 $m^2$/g.

In still yet other embodiments, the HPCM of the invention has an average pore diameter of about 20 to 1500 Å; about 50 to 1000 Å; about 100 to 750 Å; or about 150 to 500 Å.

In still yet other aspects, when the HPCM of the invention is in the form of a particle, the HPCM of the invention has an average particle size of about 0.3-100 μm; about 0.5-20 μm; 0.8-10 μm; or about 1.0-3.5 μm.

In another embodiment, the HPCM of the invention is hydrolytically stable at a pH of about 1 to about 14; at a pH of about 10 to about 14; or at a pH of about 1 to about 5.

In another aspect, the invention provides materials as described herein wherein the HPCM material further comprises a nanoparticle or a mixture of more than one nanoparticles dispersed within the chromatographic surface.

The term "nanoparticle" is a microscopic particle/grain or microscopic member of a powder/nanopowder with at least one dimension less than about 100 nm, e.g., a diameter or particle thickness of less than about 100 nm (0.1 mm), which may be crystalline or noncrystalline. Nanoparticles have properties different from, and often superior to those of conventional bulk materials including, for example, greater strength, hardness, ductility, sinterability, and greater reactivity among others. Considerable scientific study continues to be devoted to determining the properties of nanomaterials, small amounts of which have been synthesized (mainly as nano-size powders) by a number of processes including colloidal precipitation, mechanical grinding, and gas-phase nucleation and growth. Extensive reviews have documented recent developments in nano-phase materials, and are incorporated herein by reference thereto: Gleiter, H. (1989) "Nano-crystalline materials," Prog. Mater. Sci. 33:223-315 and Siegel, R. W. (1993) "Synthesis and properties of nano-phase materials," Mater. Sci. Eng. A168:189-197. In certain embodiments, the nanoparticles comprise oxides or nitrides of the following: silicon carbide, aluminum, diamond, cerium, carbon black, carbon nanotubes, zirconium, barium, cerium, cobalt, copper, europium, gadolinium, iron, nickel, samarium, silicon, silver, titanium, zinc, boron, and mixtures thereof. In certain embodiments, the nanoparticles of the present invention are selected from diamonds, zirconium oxide (amorphous, monoclinic, tetragonal and cubic forms), titanium oxide (amorphous, anatase, brookite and rutile forms), aluminum (amorphous, alpha, and gamma forms), and boronitride (cubic form). In particular embodiments, the nanoparticles of the present invention are selected from nano-diamonds, silicon carbide, titanium dioxide (anatase form), cubic-boronitride, and any combination thereof. Moreover, in particular embodiments, the nanoparticles may be crystalline or amorphous. In particular embodiments, the nanoparticles are less than or equal to 100 mm in diameter, e.g., less than or equal to 50 mm in diameter, e.g., less than or equal to 20 mm in diameter.

Moreover, it should be understood that the nanoparticles that are characterized as dispersed within the composites of the invention are intended to describe exogenously added nanoparticles. This is in contrast to nanoparticles, or formations containing significant similarity with putative nanoparticles, that are capable of formation in situ, wherein, for example, macromolecular structures, such as particles, may comprise an aggregation of these endogenously created.

In certain embodiments, the nanoparticle is present in <20% by weight of the nanocomposite, <10% by weight of the nanocomposite, or <5% by weight of the nanocomposite.

In other embodiments, the nanoparticle is crystalline or amorphous and may be silicon carbide, aluminum, diamond, cerium, carbon black, carbon nanotubes, zirconium, barium, cerium, cobalt, copper, europium, gadolinium, iron, nickel, samarium, silicon, silver, titanium, zinc, boron, oxides thereof, or a nitride thereof. In particular embodiments, the nanoparticle is a substance which comprises one or more moieties selected from the group consisting of nano-diamonds, silicon carbide, titanium dioxide, and cubic-boronitride. In other embodiments, the nanoparticles may be less than or equal to 200 nm in diameter, less than or equal to 100 nm in diameter, less than or equal to 50 nm in diameter, or less than or equal to 20 nm in diameter.

The HPCM materials of the invention may further be surface modified.

"Surface modifiers" include (typically) organic functional groups which impart a certain chromatographic functionality to a chromatographic stationary phase. The porous inorganic/organic hybrid materials possess both organic groups and silanol groups which may additionally be substituted or derivatized with a surface modifier.

The language "surface modified" is used herein to describe the composite material of the present invention that possess both organic groups and silanol groups which may additionally be substituted or derivatized with a surface modifier. "Surface modifiers" include (typically) organic functional groups which impart a certain chromatographic functionality to a chromatographic stationary phase. Surface modifiers such as disclosed herein are attached to the base material, e.g., via derivatization or coating and later cross-linking, imparting the chemical character of the surface modifier to the base material. In one embodiment, the organic groups of a hybrid material, react to form an organic covalent bond with a surface modifier. The modifiers can form an organic covalent bond to the material's organic group via a number of mechanisms well known in organic and polymer chemistry including but not limited to nucleophilic, electrophilic, cycloaddition, free-radical, carbene, nitrene, and carbocation reactions. Organic covalent bonds are defined to involve the formation of a covalent bond between the common elements of organic chemistry including but not limited to hydrogen, boron, carbon, nitrogen, oxygen, silicon, phosphorus, sulfur, and the halogens. In addition, carbon-silicon and carbon-oxygen-silicon bonds are defined as organic covalent bonds, whereas silicon-oxygen-silicon bonds that are not defined as organic covalent bonds. A variety of synthetic transformations are well known in the literature, see, e.g., March, J. Advanced Organic Chemistry, 3rd Edition, Wiley, New York, 1985.

Thus, in one embodiment, the material as described herein may be surface modified with a surface modifier having the formula $Z_a(R')_b Si-R''$, where $Z=Cl$, Br, I, $C_1$-$C_5$ alkoxy, dialkylamino or trifluoromethanesulfonate; a and b are each an integer from 0 to 3 provided that a+b=3; R' is a $C_1$-$C_6$ straight, cyclic or branched alkyl group, and R" is a functionalizing group.

In another embodiment, the materials have been surface modified by coating with a polymer.

In certain embodiments, R' is selected from the group consisting of methyl, ethyl, propyl, isopropyl, butyl, t-butyl, sec-butyl, pentyl, isopentyl, hexyl and cyclohexyl. In other embodiments, R' is selected from the group consisting of alkyl, alkenyl, alkynyl, aryl, cyano, amino, diol, nitro, ester, a cation or anion exchange group, an alkyl or aryl group containing an embedded polar functionality and a chiral moiety. In certain embodiments, R' is selected from the group consisting of aromatic, phenylalkyl, fluoroaromatic, phenylhexyl, pentafluorophenylalkyl and chiral moieties.

In one embodiment, R" is a $C_1$-$C_{30}$ alkyl group. In a further embodiment, R" comprises a chiral moiety. In another further embodiment, R" is a $C_1$-$C_{20}$ alkyl group.

In certain embodiments, the surface modifier comprises an embedded polar functionality. In certain embodiments, such embedded polar functionality includes carbonate, amide, urea, ether, thioether, sulfinyl, sulfoxide, sulfonyl, thiourea, thiocarbonate, thiocarbamate, ethylene glycol, heterocyclic, or triazole functionalities. In other embodiments, such embedded polar functionality includes carbamate functionalities such as disclosed in U.S. Pat. No. 5,374,755, and chiral moieties. Such groups include those of the general formula

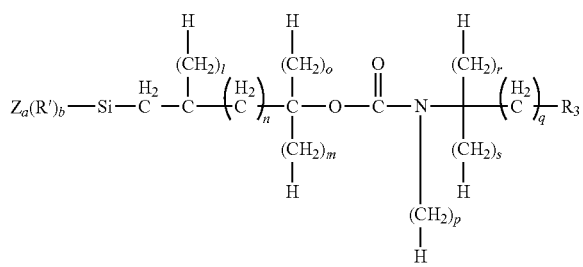

wherein l, m, o, r and s are 0 or 1, n is 0, 1, 2 or 3 p is 0, 1, 2, 3 or 4 and q is an integer from 0 to 19; $R^3$ is selected from the group consisting of hydrogen, alkyl, cyano and phenyl; and Z, R', a and b are defined as above. Preferably, the carbamate functionality has the general structure indicated below:

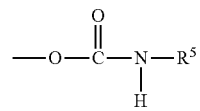

wherein $R^5$ may be, e.g., cyanoalkyl, t-butyl, butyl, octyl, dodecyl, tetradecyl, octadecyl, or benzyl. Advantageously, $R^5$ is octyl, dodecyl, or octadecyl.

In certain embodiments, the surface modifier is selected from the group consisting of phenylhexyltrichlorosilane, pentafluorophenylpropyltrichlorosilane, octyltrichlorosilane, octadecyltrichlorosilane, octyldimethylchlorosilane and octadecyldimethylchlorosilane. In some embodiments, the surface modifier is selected from the group consisting of octyltrichlorosilane and octadecyltrichlorosilane. In other embodiments, the surface modifier is selected from the group consisting of an isocyanate or 1,1'-carbonyldiimidazole (particularly when the hybrid group contains a $(CH_2)_3$ OH group).

In another embodiment, the material has been surface modified by a combination of organic group and silanol group modification.

In still another embodiment, the material has been surface modified by a combination of organic group modification and coating with a polymer. In a further embodiment, the organic group comprises a chiral moiety.

In yet another embodiment, the material has been surface modified by a combination of silanol group modification and coating with a polymer.

In other embodiments, the material has been surface modified via formation of an organic covalent bond between the particle's organic group and the modifying reagent.

In still other embodiments, the material has been surface modified by a combination of organic group modification, silanol group modification and coating with a polymer.

In another embodiment, the material has been surface modified by silanol group modification.

In certain embodiments, the surface modified layer may be porous or non-porous.

Another aspect provides a variety of separations devices having a stationary phase comprising the HPCM materials as described herein. The separations devices include, e.g., chromatographic columns, thin layer plates, filtration membranes, sample cleanup devices and microtiter plates.

The HPCM Materials impart to these devices improved lifetimes because of their improved stability. Thus, in a particular aspect, the invention provides a chromatographic column having improved lifetime, comprising a) a column having a cylindrical interior for accepting a packing material, and b) a packed chromatographic bed comprising the high purity chromatographic material as described herein.

In another particular aspect, the invention provides a chromatographic device, comprising a) an interior channel for accepting a packing material and b) a packed chromatographic bed comprising the high purity chromatographic material as described herein.

The invention also provides for a kit comprising the HPCM materials as described herein, as described herein, and instructions for use. In one embodiment, the instructions are for use with a separations device, e.g., chromatographic columns, thin layer plates, filtration membranes, sample cleanup devices and microtiter plates.

Mass Spectroscopy

Further to the summary above, the technology includes analyzing the component of the first fraction by mass spectroscopy, thereby identifying the polypeptide, if present, using a signal corresponding to a sequence fragment ion from the polypeptide. The analysis step of the technology works in concert with the pre-treatment and separation steps, to provide a high resolution tool for studying polypeptides.

In general, the first fraction should include a sequence that is indicative of, and specific to the polypeptide analyte. For example, the component of the first fraction can include the polypeptide analyte in an undigested, or essentially undigested, state.

Accordingly, MS analysis can produce a sequence fragment ion from the polypeptide that is indicative of, and specific to the polypeptide analyte. For example, the signal corresponds to an intact multiply charged precursor fragment selected in a first quadrupole and its corresponding sequence fragment ion selected in a final quadrupole. In the examples of insulin discussed below, the sequence fragment ion exhibits an m/z >800. Where the method is used on another polypeptide, the sequence fragment ion can exhibit an m/z that is characteristic of that polypeptide in an undigested, or essentially undigested state. In an alternative embodiment, the polypeptide can be digested, as long as the sequence fragment ion is indicative of, and specific to the polypeptide analyte.

In some embodiments (e.g., where one might typically rely on a single precursor to generate fragments for small molecule analyses), there can be advantages to selecting multiple precursors to attempt fragmentation of a peptide analyte. Not only can the various charge states fragment differently, but it can be difficult to predict the specificity of a particular MRM in a sample derived from a biological matrix. Furthermore, there can exist some question as to whether or not the relative abundance of the various charge states changes during analysis, driving the desire to monitor and possibly sum MRMs arising from distinct precursors.

FIGS. 22A-22D shows an MS spectrum for four synthetic insulin analogs, Lantus® (insulin glargine), Levemir® (insulin detemir), Novolog/NovoRapid® (insulin aspart), and Apidra® (insulin glulisine). Note that each analog yields a unique selection and pattern of precursors, despite their closely related chemical nature. In some embodiments, for each analog, the two or three most abundant precursors were chosen for fragmentation. CID of the chosen precursors was performed over the range of m/z 100-1800. Both the 6+ and 7+ insulin glargine precursors yielded multiple possible fragments, whereas only the 6+ charge state of insulin aspart and the 5+ of glulisine and detemir resulted in fragment ions with sufficient intensity for meaningful quantification. Representative MSMS spectra for each insulin analog at its optimum collision energy is shown in FIGS. 22A-22D. Fragments chosen for quantification are highlighted with an asterisk.

In some embodiments, under low resolution conditions, there is overlap between the isotope patterns of the 5+ and 6+ multiply charged precursors of aspart and glulisine (see FIGS. 1, 8A, 13 and 17). This can lead to a lack of specificity if unique fragments are not chosen. In some embodiments, these same precursors can also overlap with human insulin. However, certain fragments arising from human insulin (e.g., at m/z 561, 653, and 226) are also unique (data not shown). At higher collision energies, each of the insulin analogs can produce immonium ion fragments with high intensity. Most yield an intense peak m/z 136, for example, corresponding to a tyrosine immonium ion. These spectra are simpler than the MSMS spectra for the insulins at their optimal, lower collision energies and they are dominated by a single intense fragment, rather than several low intensity fragments. In some embodiments, the choice of peptide fragment ion is more complicated than simply choosing the most intense fragment.

In some embodiments, due to the nominal mass resolution limitations of certain triple quadrupole instruments, the high concentration of other peptides in the sample (possibly closely related), and/or the high chemical background associated with low m/z fragments, specificity in the endogenous matrix was found to be a critical deciding factor. For example, improved sensitivity was observed at higher mass ranges, facilitating the use of fragments such as the m/z 984 for glargine and m/z 1370 for glulisine in quantification. This observed specificity benefit derived from these larger fragments was central to reducing the overall demand on the sample preparation, and contributed to the use of a significantly simpler and faster sample prep scheme than previously published methods.

The mass spectrometer should also be capable of obtaining a signal corresponding to a sequence fragment ion from the polypeptide. The mass spectrometer should also be capable of achieving a desired detection limit. For example, the mass spectrometry can employ a triple quadrupole mass spectrometer. The mass spectrometry can be carried out in positive electrospray ionisation mode. In certain embodiments, the detection limit of the polypeptide of interest, for instance for insulin or an insulin analog, is 0.25 ng/mL or less. The detection limit of the polypeptide of interest can be 0.50 ng/mL or less. The detection limit can be achieved in a specimen of 250 microliters or less. In some embodiments, the detection limit of the polypeptide of interest can be 30 pg/mL or less. In some embodiments, the detection limit of the polypeptide of interest can be 15 pg/mL or less. For instance, in some embodiments, the detection limit of the polypeptide of interest can be 30 pg/mL or less, 29 pg/mL or less, 28 pg/mL or less, 27 pg/mL or less, 26 pg/mL or less, 25 pg/mL or less, 24 pg/mL or less, 23 pg/mL or less, 22 pg/mL or less, 21 pg/mL or less, 20 pg/mL or less, 19 pg/mL or less, 18 pg/mL or less, 17 pg/mL or less, 16 pg/mL or less, or 15 pg/mL or less.

The MS can employ RF transmission optics to improve sensitivity, for example by allowing the user to pull in more ions, filter non-ions, and focus the ion beam for efficient transmission. In one embodiment, the technology employs RF transmission optics by use of an LC/MS/MS apparatus.

Specificity

For a method in accordance with the invention, where several closely related large peptides (e.g., with multiple possible molecular ions) are being analyzed in complex matrix using low resolution mass spectrometry, the risk of interference from the MRM of one insulin channel into another can be high. Therefore, one must assess the contribution of analytes present individually at high concentration, to the response in other channels. In order to evaluate the specificity of the method, samples were fortified individually with one of the four analogs at a concentration of 500 ng/mL, which is 20× the plasma ULOQ of 25 ng/mL. In addition, samples were fortified with human insulin only at 500 ng/mL and 1 µg/mL to assess the impact and potential interference of high levels of endogenous insulin (as might be present in Type 2 diabetics) on assay specificity.

EXAMPLES

Unless indicated otherwise, all techniques, including the use of kits and reagents, can be carried out according to the manufacturers' information, methods known in the art, or as described, for example, in *Tietz Text Book of Clinical Chemistry* 3rd Edition (Burtis, C. A. & Ashwood, M. D., Eds.) W. B. Saunders Company, 1999; *Guidance for Industry. Bioanalytical Method Validation*. USA: Centre for Drug Evaluation and Research, US Department of Health and Social Services, Food and Drug Administration, 2001; and Sambrook et al., *Molecular Cloning. A Laboratory Manual*, 2nd Edition (1989) Cold Spring Harbor Laboratory Press, Cold Spring Harbor, N.Y.

In the following four examples, four synthetic insulin analogs, Lantus® (insulin glargine), Levemir® (insulin detemir), Novolog/NovoRapid® (insulin aspart), and Apidra® (insulin glulisine), were analyzed in human plasma samples. The fifth example is an example illustrating the use of this technology with a sample of human plasma obtained from a subject to measure a generic analyte of interest.

Samples were prepared by spiking the synthetic insulin analogs, Lantus® (insulin glargine), Levemir® (insulin detemir), Novolog/NovoRapid® (insulin aspart), and Apidra® (insulin glulisine), in human plasma to final concentrations of between 50 pg/mL and 500 ng/mL.

Treatment and extraction of the samples was carried out on a micro elution 96-well plate designed for solid phase extraction and having a hydrophilic-lipophilic-balanced reversed-phase sorbent and conditioned with 200 µL methanol and equilibrated with 200 µL water. Samples were diluted with 250 µL 10 mM TRIS base (2-amino-2-hydroxymethyl-propane-1,3-diol) and then loaded onto the plate. The plates were washed with 200 µL 5% methanol, 1% acetic acid in water; eluted with 2×25 µL 60% methanol, 10% acetic acid in water; and diluted with 50 µL water. Recoveries ranged from 82-95%.

Separation was carried out on an ultra high performance liquid chromatography apparatus with a flow-through needle auto sampler using an ultra high-performance liquid chromatography column (2.1×50 mm, 1.7 µm) wherein the chromatographic surface includes a hydrophobic surface group and one or more ionizable modifiers using the following parameters—Mobile Phase A: 0.1% formic acid in water; Mobile Phase B: 0.1% formic acid in acetonitrile; Weak wash: mobile phase A; Strong wash: 50/25/24/1 ACN/IPA/water/formic acid; Flow rate: 0.3 mL/min; Column temperature: 45° C.; Sample Manager temperature: 15° C.; Gradient: 20% B to 65% B in 2 min, to 98% B at 2.1 min, hold for 0.5 min, return to initial at 2.7 min; Total cycle time: 3.5 min; Injection solvent: methanol and acetic acid; and Injection volume: 10 µL. Representative standard curve statistics for insulin glulisine (A) and insulin glargine (B) from 50 pg/mL to 500 ng/mL in solvent standards are shown below in Table 1A and 1B:

TABLE 1A

Representative standard curve statistics for insulin glulisine from 50 pg/mL to 500 ng/mL in solvent standards

| Name | Expected Conc. (ng/mL) | Area | Calc. Conc. (ng/mL) | % Dev. |
|---|---|---|---|---|
| 50 pg/mL | 0.05 | 246.6 | 0.045 | −9.5 |
| 100 pg/mL | 0.1 | 563.7 | 0.101 | 1 |
| 200 pg/mL | 0.2 | 1090 | 0.194 | −3.2 |
| 500 pg/mL | 0.5 | 2642.8 | 0.467 | −6.7 |
| 1 ng/mL | 1 | 5544.9 | 0.977 | −2.3 |
| 2 ng/mL | 2 | 11120.5 | 1.957 | −2.1 |
| 5 ng/mL | 5 | 28094.9 | 4.942 | −1.2 |
| 10 ng/mL | 10 | 61467.9 | 10.811 | 8.1 |
| 20 ng/mL | 20 | 117881.6 | 20.731 | 3.7 |
| 50 ng/mL | 50 | 298668.7 | 52.523 | 5 |
| 100 ng/mL | 100 | 625570.8 | 110.009 | 10 |
| 500 ng/mL | 500 | 2764219.3 | 486.092 | −2.8 |

TABLE 1B

Representative standard curve statistics for insulin glargine from 50 pg/mL to 500 ng/mL in solvent standards

| Name | Expected Conc. (ng/mL) | Area | Calc. Conc. (ng/mL) | % Dev |
|---|---|---|---|---|
| 50 pg/mL | 0.05 | 483.06 | 0.051 | 2.4 |
| 100 pg/mL | 0.1 | 777.31 | 0.094 | −6.4 |
| 500 pg/mL | 0.5 | 3748.09 | 0.522 | 4.3 |
| 1 ng/mL | 1 | 6955.55 | 0.984 | −1.6 |
| 2 ng/mL | 2 | 15881.66 | 2.27 | 13.5 |
| 5 ng/mL | 5 | 38498.98 | 5.528 | 10.6 |
| 10 ng/mL | 10 | 74175.04 | 10.668 | 6.7 |
| 20 ng/mL | 20 | 143202.70 | 20.612 | 3.1 |
| 50 ng/mL | 50 | 308271.28 | 44.393 | −11.2 |
| 500 ng/mL | 500 | 2734696.00 | 393.954 | −21.2 |

MS analysis was carried out on a triple quadrupole MS using the following parameters—Capillary: 3.00 kV; Desolvation temperature: 600° C.; Source temperature: 150° C. Desolvation flow: 1000 L/hr; and the insulin analog-specific MRM transitions listed below. MassLynx™ software was used for data acquisition. All peak area integration, regression analysis and sample quantification was performed using TargetLynx™ software. Peak area ratios (PARs) of the insulin analogs and the bovine insulin internal standard were determined and calibration curves generated for each of the analogs. Insulin analog concentrations in QC samples were determined from their PARs against their respective calibration lines.

Example 1

Lantus® (Insulin Glargine)

Samples were treated, extracted, separated, and analyzed as described above. The results are shown and discussed in connection with FIGS. 1-7A-7E below. Analysis of Lantus® (insulin glargine) used the MRM transitions shown in Table 2 below:

TABLE 2

MRM transitions for Lantus ® (insulin glargine).

| MRM Transition | Cone Voltage (V) | Collision Energy (eV) |
|---|---|---|
| 867 –> 856 | 60 | 18 |
| 867 –> 984 | 60 | 18 |
| 1011 –> 1164 | 60 | 25 |
| 1011 –> 1179 | 60 | 25 |

The 867→984 transition was used for quantitation of Lantus® (insulin glargine) based upon MS tuning studies, low detection limit, and linearity.

Figure 2:
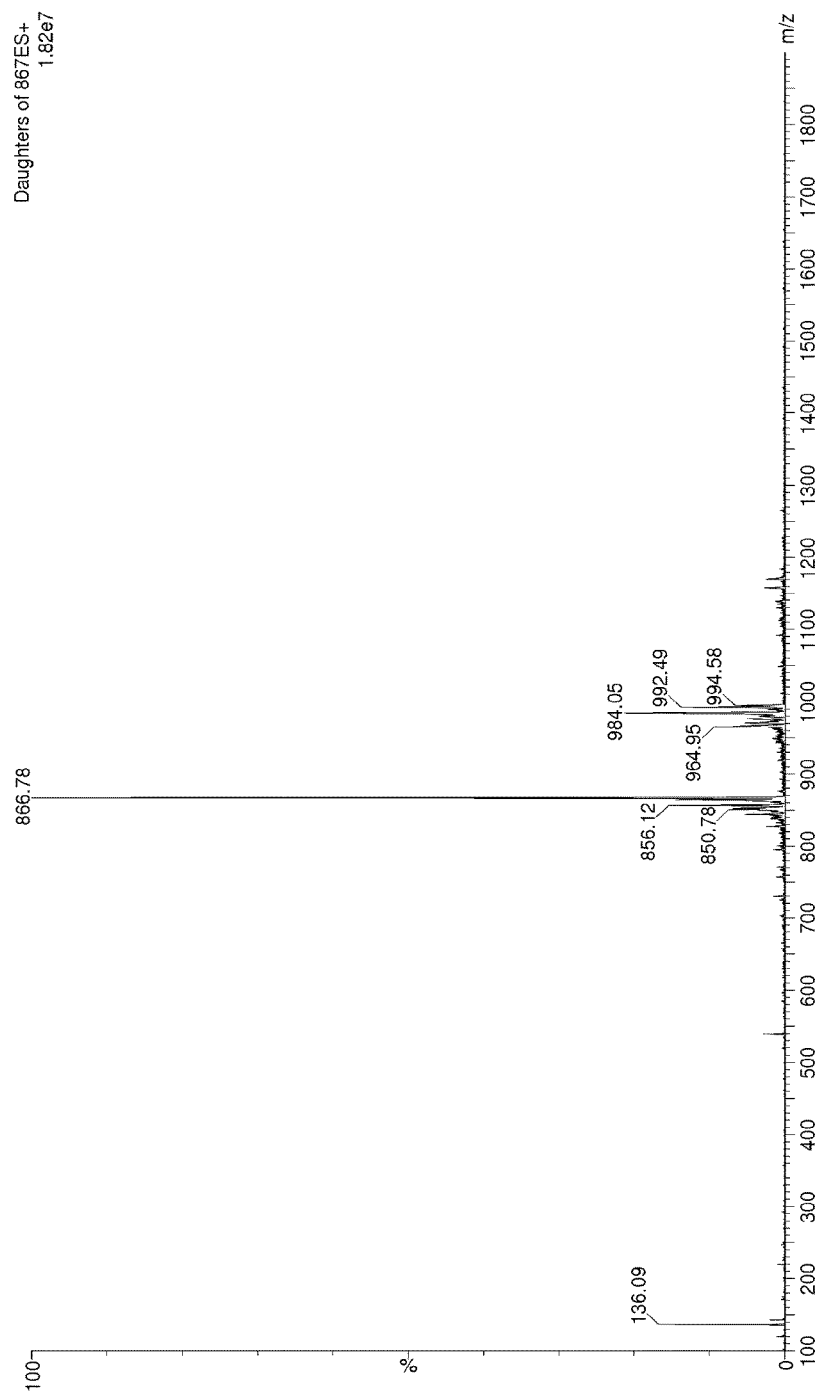
FIG. 2 shows a MS/MS scan of m/z 867 for Lantus® (insulin glargine).
Figure 3:
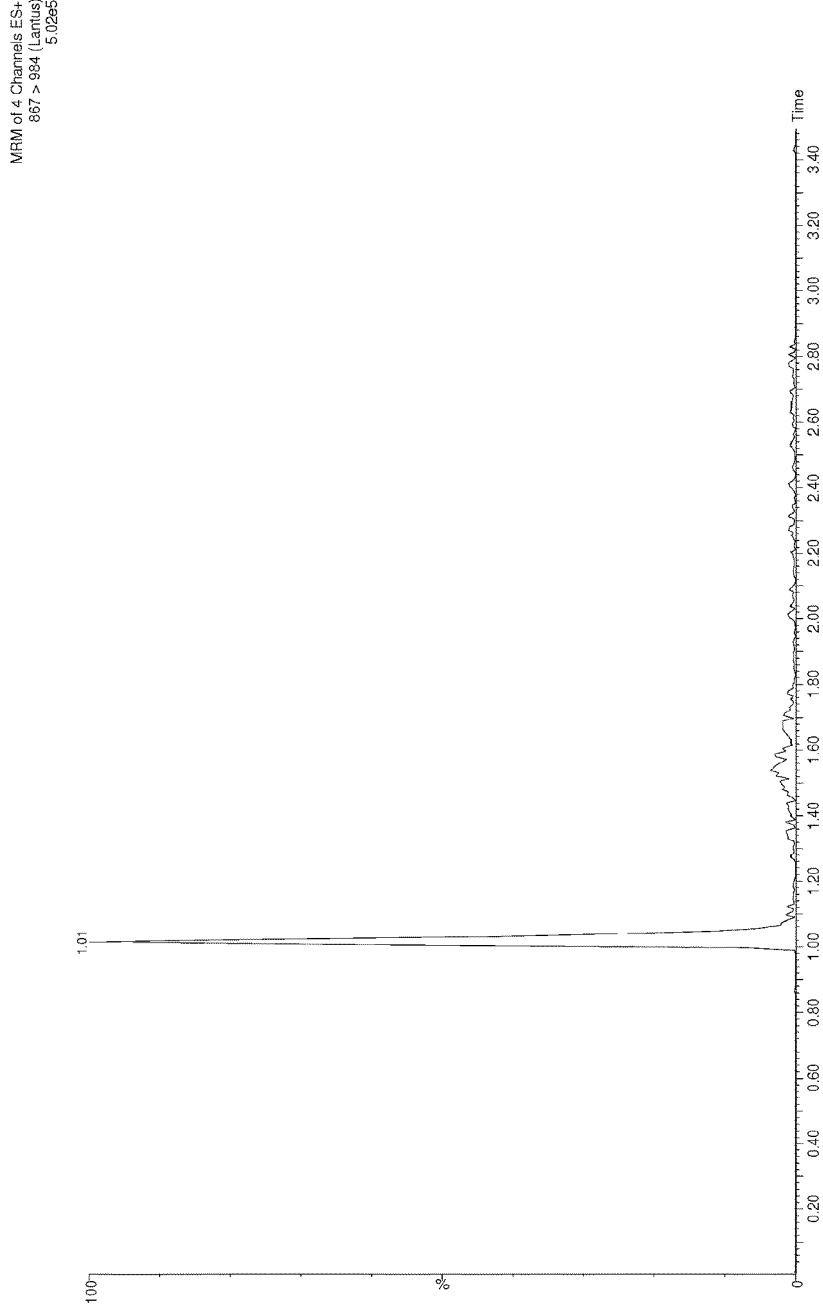
FIG. 3 shows a chromatogram for the transition monitoring of Lantus® (insulin glargine).

FIG. 1 shows a MS scan of Lantus® (insulin glargine) with the 8+, 7+, 6+, and 5+ transitions annotated. FIG. 2 shows a MS/MS scan of m/z 867, which is the 7+ precursor of Lantus® (insulin glargine). FIG. 3 shows a chromatogram for the 867→984 transition monitoring for Lantus® (insulin glargine) (the A chain plus a y19 B chain ion type) using a 2 ng/mL standard solution (peak width 3.6 s).

Figure 4D:
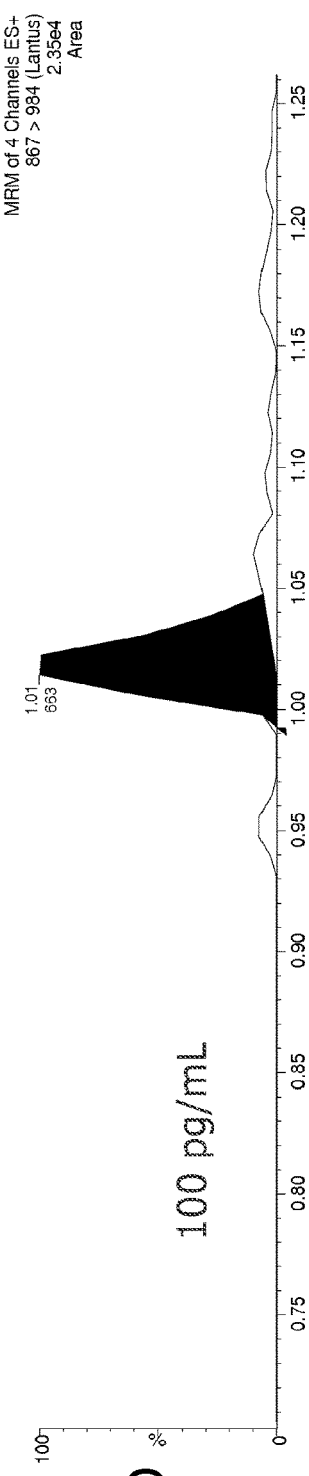
FIGS. 4D-4F shows integrated analyte peaks from the chromatograms shown in FIGS. 4A-4C.
Figure 4E:
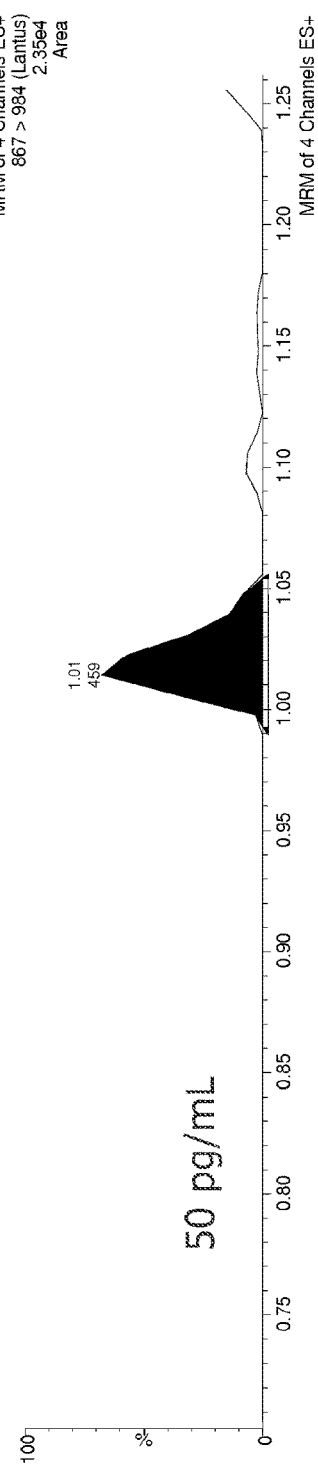
Figure 4F:
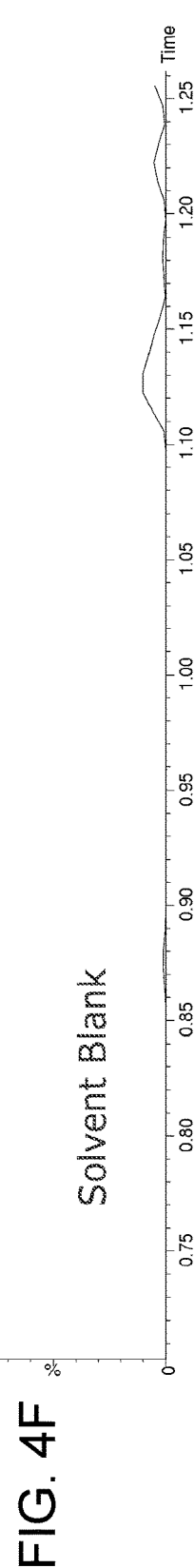

FIG. 4A shows chromatograms for 100 pg/mL (top panel) and FIG. 4B shows 50 pg/mL (middle panel) of Lantus® (insulin glargine) and FIG. 4C shows solvent blank (bottom panel). 30% methanol, 10% acetic acid, and 0.05% rat plasma was used as a dilution solvent. FIGS. 4D-4F shows integrated analyte peaks from the chromatograms shown in FIGS. 4A-4C. The detection limit was 50 pg/mL. FIGS. 5A-5C shows the linearity for Lantus® (insulin glargine) in solvent standards from 50 pg/mL to 500 ng/mL.

FIG. 6A shows chromatograms for 10 μL injections of 0.5 ng/mL (top panel) and 0.2 ng/mL of Lantus® (insulin glargine) extracted from human plasma and analyzed in accordance with the methods described above. FIG. 6C shows a blank of human plasma is also shown for comparison (bottom panel). FIGS. 7A-E shows chromatograms for additional levels and integration for Lantus® (insulin glargine). Concentrations shown are 5 ng/mL (top panel), FIG. 7A, 1 ng/mL (second panel from top), FIG. 7B, 0.5 ng/mL (middle panel), FIG. 7C, 0.2 ng/mL (second from bottom), FIG. 7D, and blank human plasma (bottom panel) FIG. 7E.

Example 2

Levemir® (Insulin Detemir)

Samples were treated, extracted, separated, and analyzed as described above. The results are shown and discussed in connection with FIGS. 8A-12A-12C below. Analysis of Levemir® (insulin detemir) used the MRM transitions shown in Table 3 below:

TABLE 3

MRM transitions for Levemir ® (insulin detemir).

| MRM Transition | Cone Voltage (V) | Collision Energy (eV) |
|---|---|---|
| 1184 –> 454.4 | 60 | 20 |
| 1183.8 –> 1366.3 | 60 | 20 |

The 1184→454.4 transition was used for quantitation of Levemir® (insulin detemir) (a y2 type ion) based upon MS tuning studies, low detection limit, and linearity.

Figure 8A:
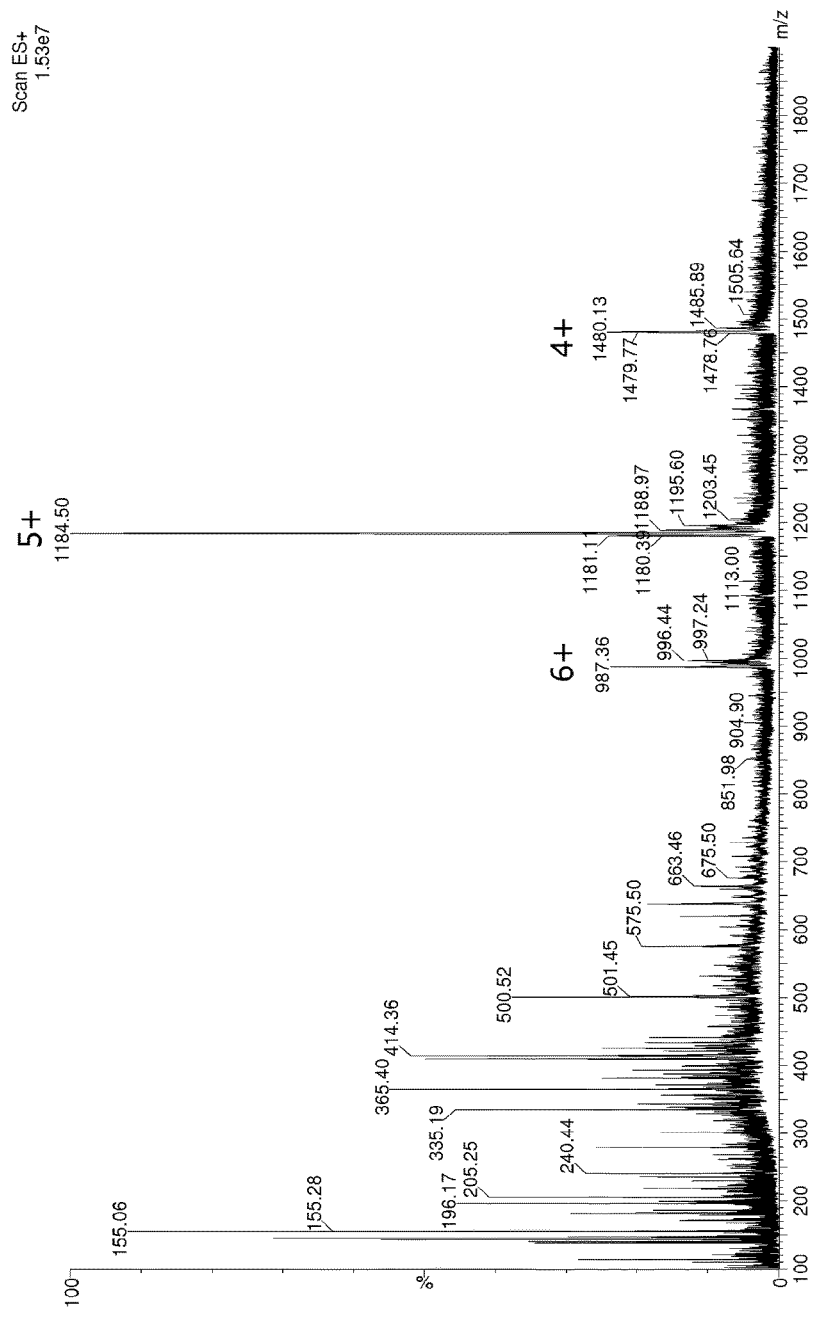
FIG. 8A shows a MS scan of Levemir® (insulin detemir).
Figure 8B:
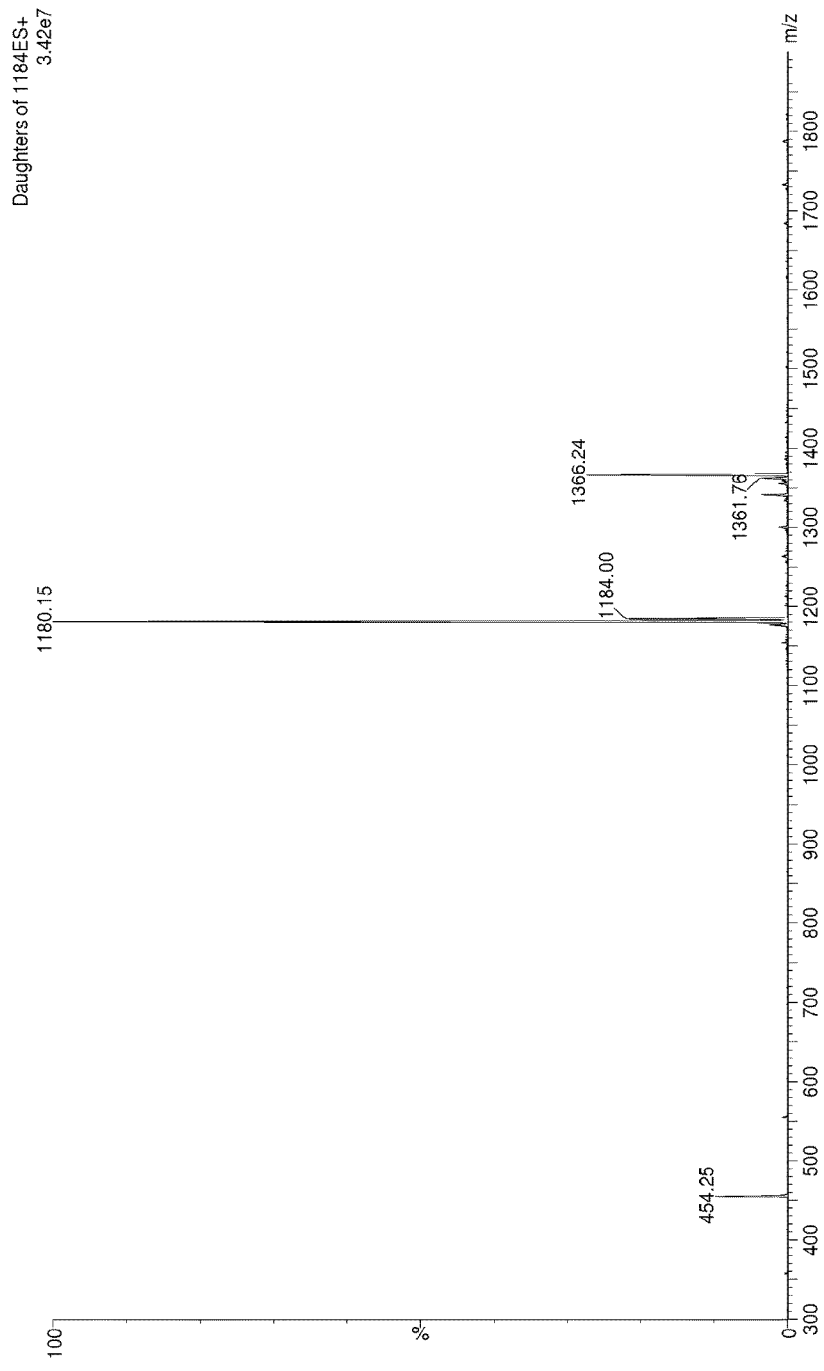
FIG. 8B shows a MS/MS scan of m/z 1184 for Levemir® (insulin detemir).

FIG. 8A shows a MS scan of Levemir® (insulin detemir) with the 6+, 5+, and 4+ transitions annotated. FIG. 8B shows a MS/MS scan of m/z 1184, which is the 5+ precursor of Levemir® (insulin detemir).

Figure 9A:
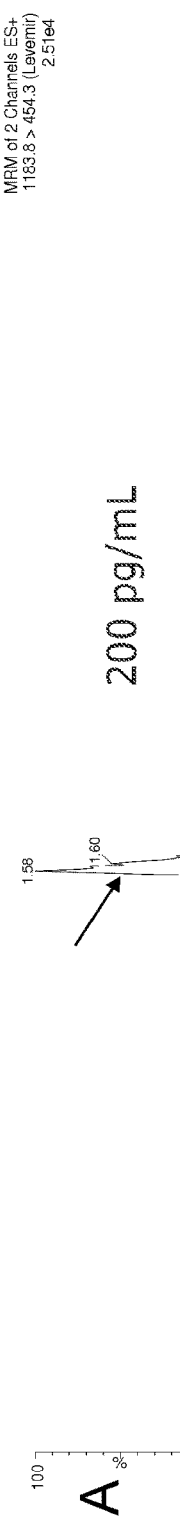
FIGS. 9A-9D shows chromatograms for Levemir® (insulin detemir) at various concentrations.
Figure 9B:
Figure 9C:
Figure 9D:
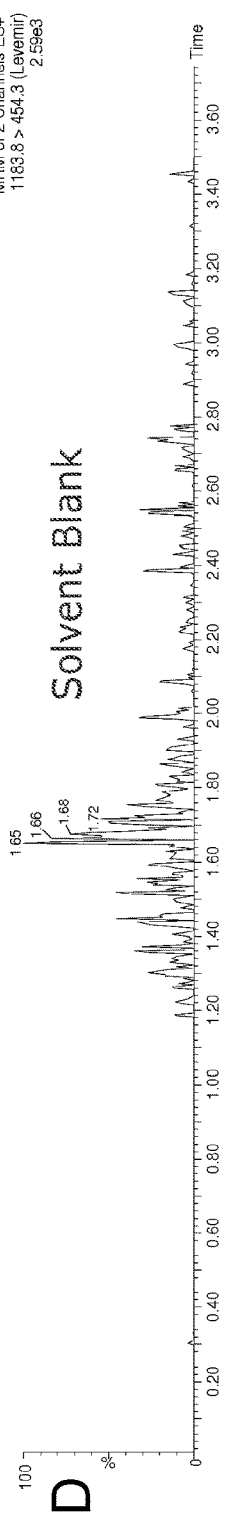
Figure 9E:
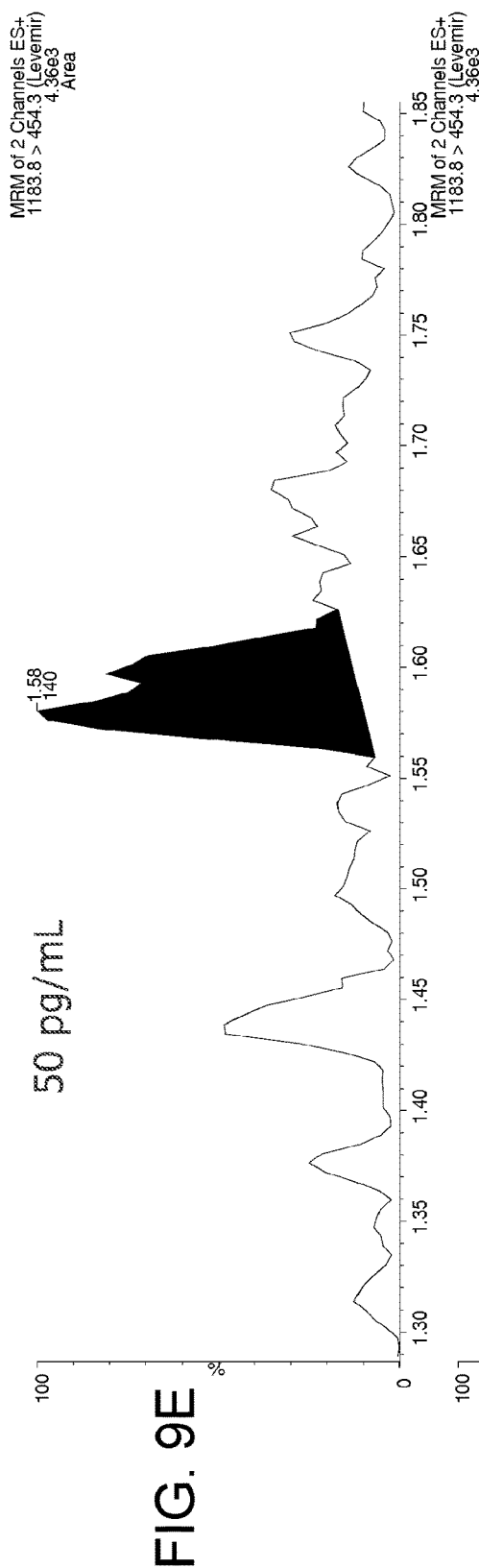
FIGS. 9E-9F shows an integrated analyte peak from the chromatograms shown in FIGS. 9A-9D.
Figure 9F:
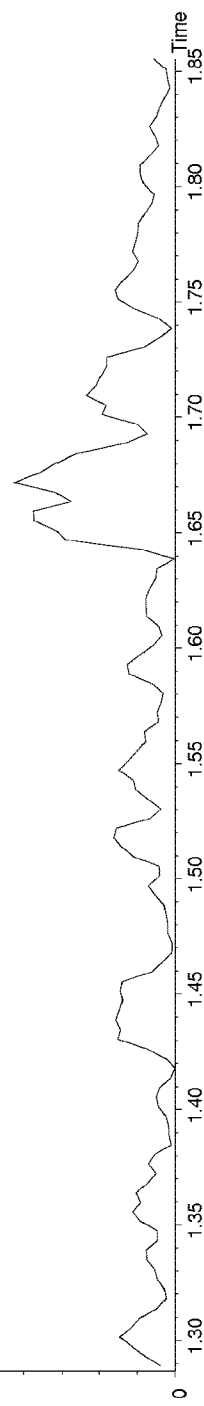
Figures 10A, 10B, 10C:
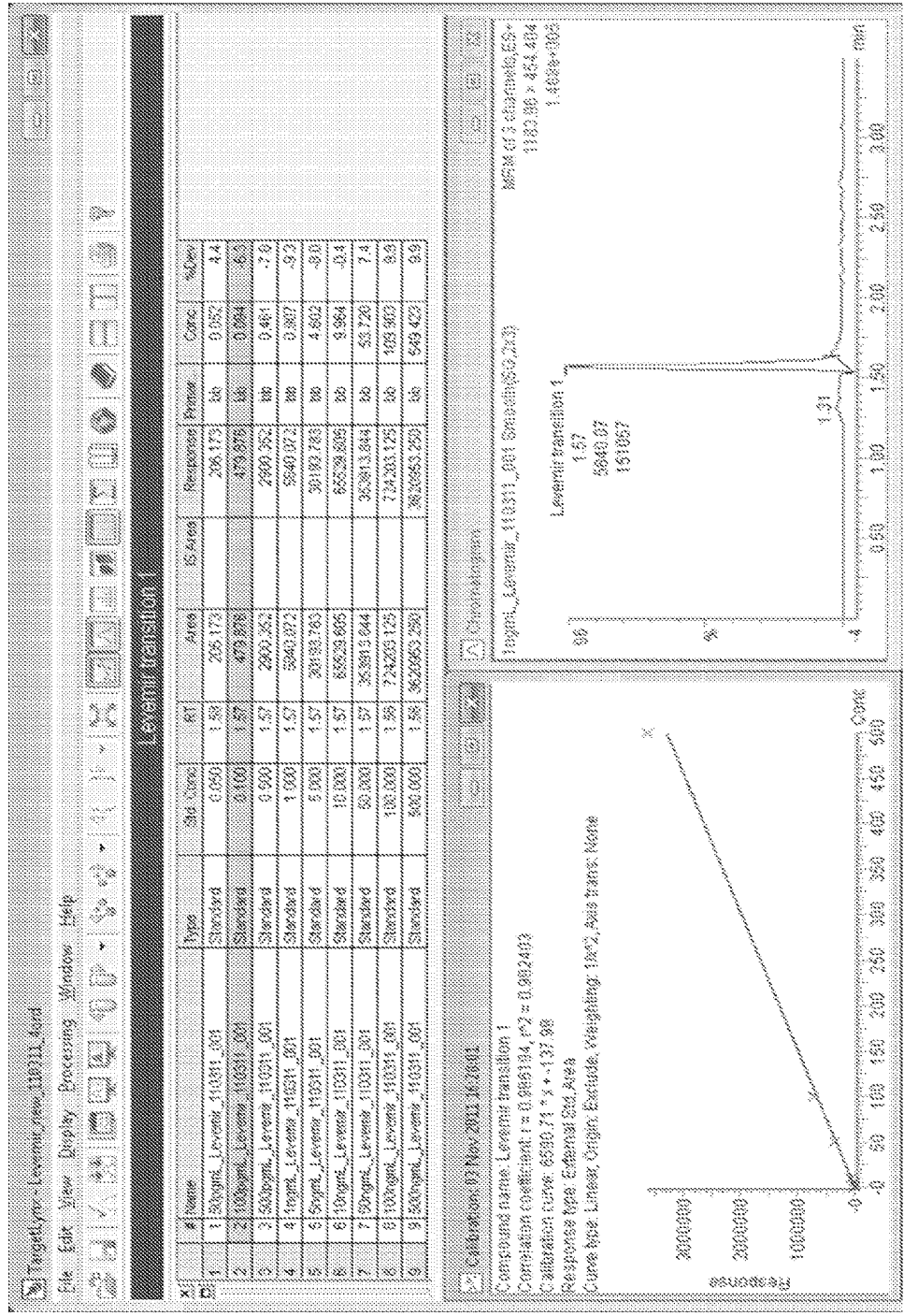
FIGS. 10A-10C shows the linearity for Levemir® (insulin detemir) in solvent standards.

FIG. 9A shows chromatograms for 200 pg/mL (top panel), 100 pg/mL (second panel from top), FIG. 9B, and 50 pg/mL (second panel from bottom), FIG. 9C, of Levemir® (insulin detemir) and solvent blank (bottom panel), FIG. 9D. 30% methanol, 10% acetic acid, and 0.05% rat plasma was used as a dilution solvent. FIGS. 9E-9F shows an integrated analyte peak from the chromatograms shown in FIGS. 9A-9D. The detection limit was 50 pg/mL. FIGS. 10A-10C shows the linearity for Levemir® (insulin detemir) in solvent standards from 50 pg/mL to 500 ng/mL.

Figures 11A, 11B, 11C:
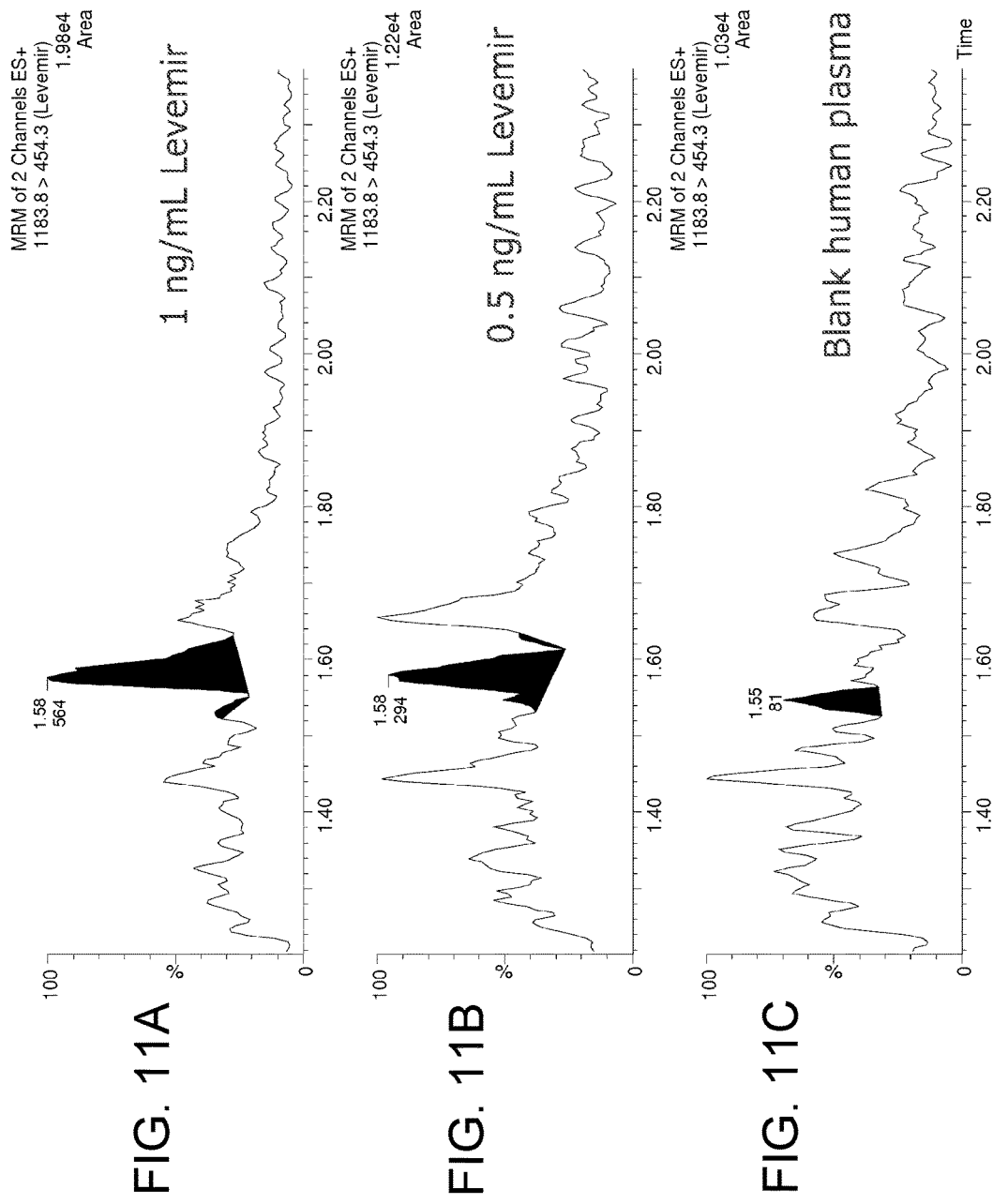
FIGS. 11A-11C shows chromatograms and peak integrations for Levemir® (insulin detemir) extracted from human plasma and analyzed in accordance with the technology.

FIG. 11A shows chromatograms and peak integrations from 10 μL injections of 1 ng/mL (top panel), and 0.5 ng/mL (middle panel), FIG. 11B extracted from human plasma and analyzed in accordance with the methods described above. A blank human plasma is also shown for comparison (bottom panel), FIG. 11C.

FIG. 12A shows chromatograms and peak integrations from 20 μL injections of 0.5 ng/mL (top panel) and 0.2 ng/mL (middle panel), FIG. 12B extracted from human plasma and analyzed in accordance with the methods described above. A blank human plasma is also shown for comparison (bottom panel), FIG. 12C.

Example 3

Apidra® (Insulin Glulisine)

Samples were treated, extracted, separated, and analyzed as described above. The results are shown and discussed in connection with FIGS. 13-16A-16C below. Analysis of Apidra® (insulin glulisine) used the MRM transitions shown in Table 4 below:

TABLE 4

MRM transitions for Apidra ® (insulin glulisine).

| MRM Transition | Cone Voltage (V) | Collision Energy (eV) |
|---|---|---|
| 1165 –> 346.2 | 14 | 22 |
| 1165 –> 1161.6 | 14 | 22 |
| 1165 –> 1369.9 | 14 | 22 |

The 1165→346.2 (a y3 type ion) or 1369.9 transitions were used for quantitation of Apidra® (insulin glulisine) based upon MS tuning studies, low detection limit, and linearity.

Figure 13:
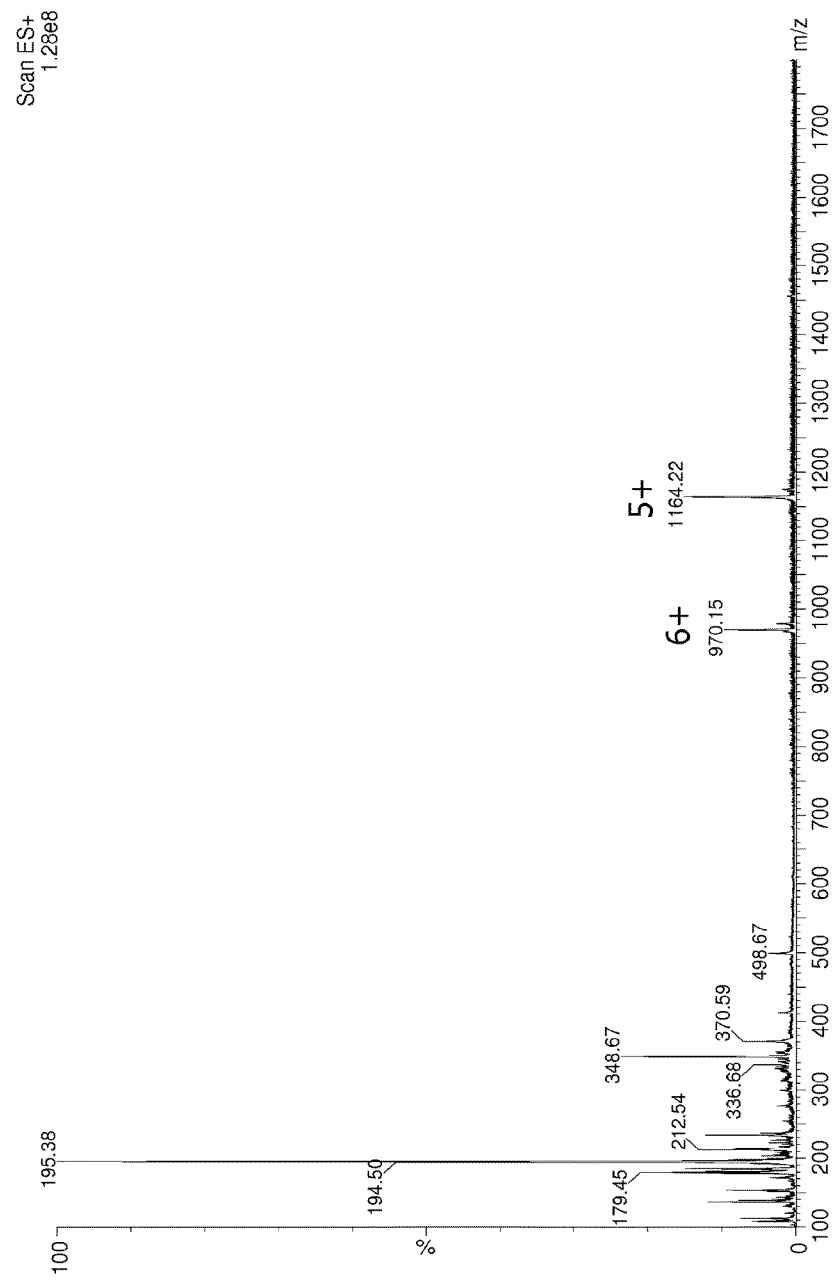
FIG. 13 shows a MS scan of Apidra® (insulin glulisine).

FIG. 13 shows a MS scan of Apidra® (insulin glulisine) with the 6+ and 5+ transitions annotated. FIG. 14A shows chromatograms for 100 pg/mL (top panel) and 50 pg/mL (middle panel), FIG. 14B of Apidra® (insulin glulisine) and blank solvent (bottom panel), FIG. 14C. The detection limit was 50 pg/mL. FIGS. 15A-15C shows the linearity for Apidra® (insulin glulisine) in solvent standards from 50 pg/mL to 500 ng/mL.

FIG. 16A shows chromatograms and peak integrations of 0.5 ng/mL (top panel), and 0.2 ng/mL (middle panel), FIG. 16B of Apidra® (insulin glulisine) extracted from human plasma and analyzed in accordance with the methods described above. A blank human plasma is also shown for comparison (bottom panel), FIG. 16C.

Example 4

Novolog/Novorapid® (Insulin Aspart)

Samples were treated, extracted, separated, and analyzed as described above. The results are shown and discussed in connection with FIGS. 17-20A-20C below. Analysis of Novolog/Novorapid® (insulin aspart) used the MRM transitions shown in Table 5 below:

TABLE 5

MRM transitions for Novolog/Novorapid ® (insulin aspart).

| MRM Transition | Cone Voltage (V) | Collision Energy (eV) |
|---|---|---|
| 971.6 –> 1139.4 | 12 | 18 |
| 971.8 –> 660.8 | 60 | 18 |
| 971.6 –> 1146 | 12 | 18 |
| 1165.7 –> 1395.4 | 88 | 28 |

The 971.8→660.8 transition (a y11 type ion) was used for quantitation of Novolog/Novorapid® (insulin aspart) based upon MS tuning studies, low detection limit, and linearity. Additionally, the 971.6-1139.4 transition gives an ion type that is A chain plus b20 B chain.

Figure 17:
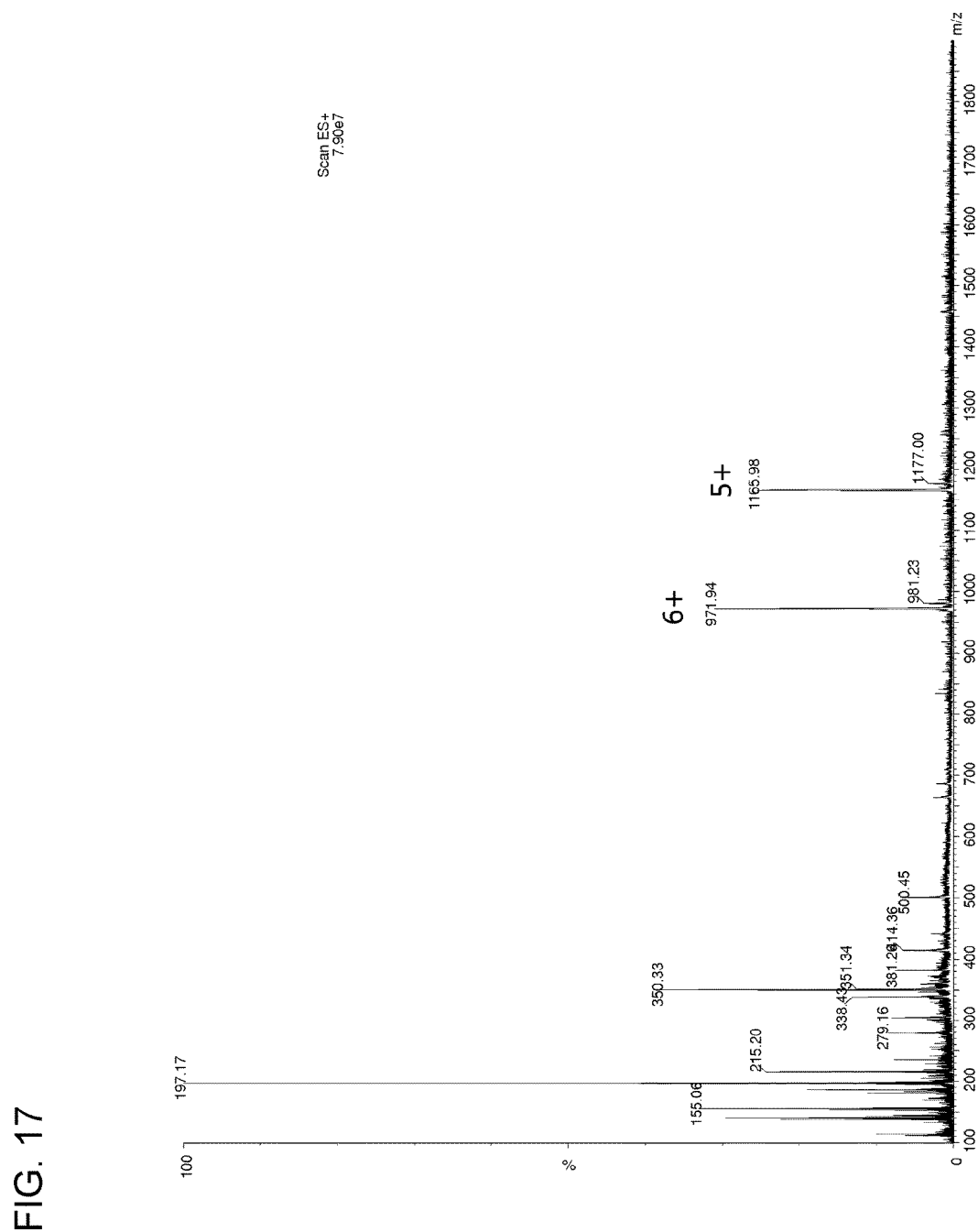
FIG. 17 shows a MS scan of Novolog/Novorapid® (insulin aspart).
Figures 18A, 18B, 18C, 18D:
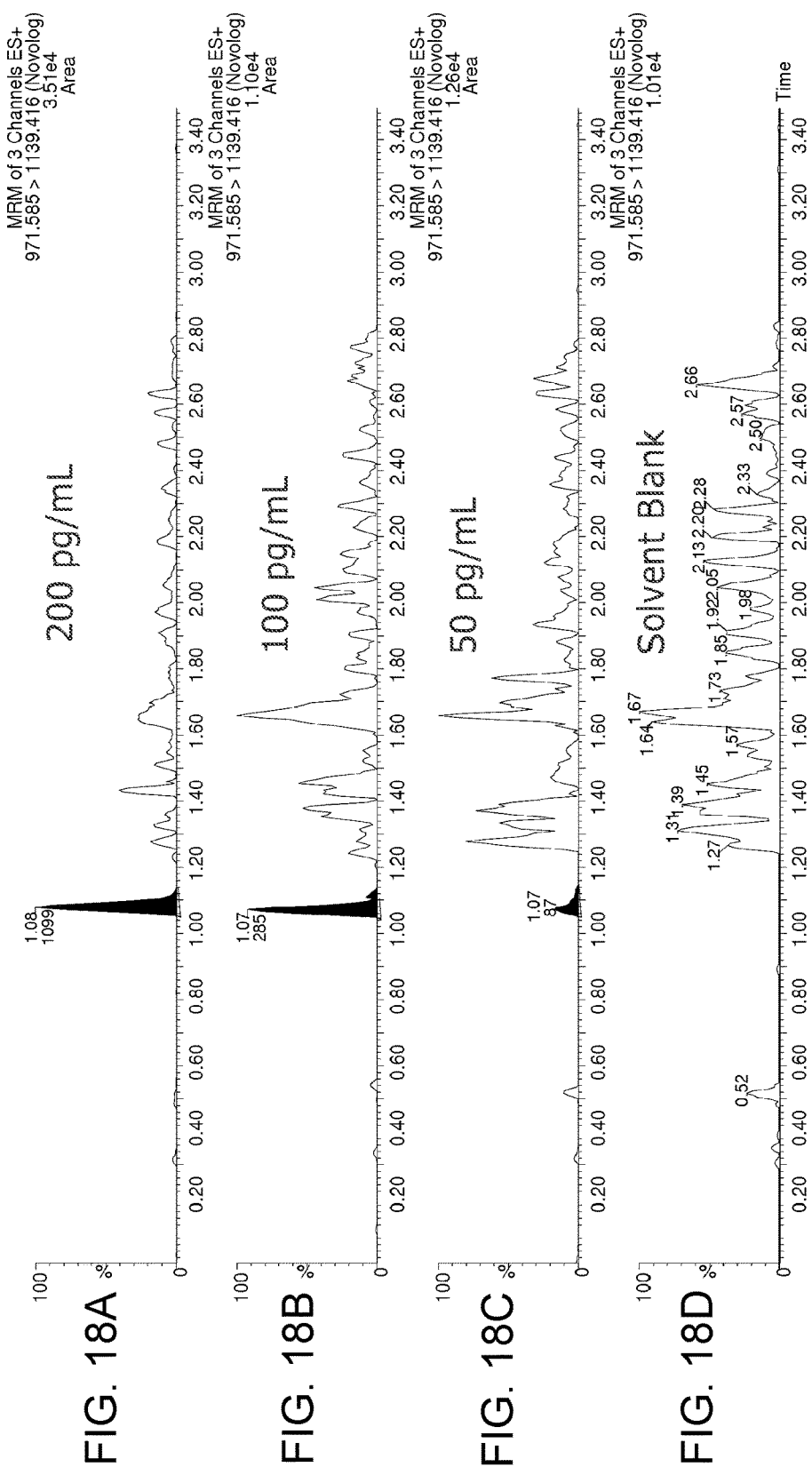
FIGS. 18A-18D shows chromatograms for Novolog/Novorapid® (insulin aspart) at various concentrations.
Figures 19A, 19B, 19C:
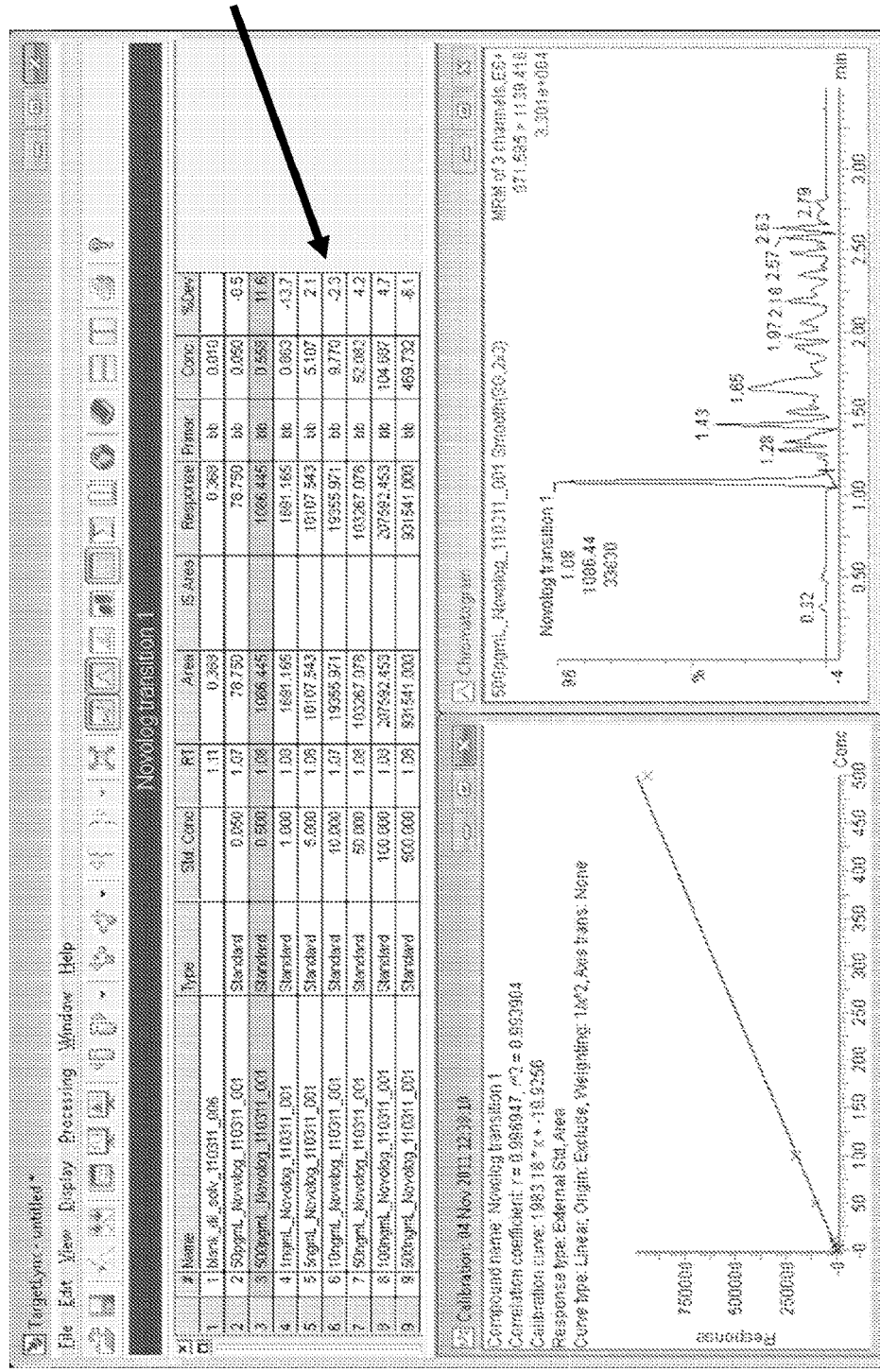
FIGS. 19A-19C shows the linearity for Novolog/Novorapid® (insulin aspart) in solvent standards.

FIG. 17 shows a MS scan of Novolog/Novorapid® (insulin aspart) with the 6+ and 5+ transitions annotated. FIG. 18A shows chromatograms for 200 pg/mL (top panel), 100 pg/mL (second panel from top), FIG. 18B, and 50 pg/mL (second panel from bottom), FIG. 18C of Novolog/Novorapid® (insulin aspart) and solvent blank (bottom panel), FIG. 18D. FIG. 18E shows an integrated analyte peak from the chromatograms shown in FIG. 18A (top panel) and solvent blank (bottom panel), FIG. 18D. The detection limit was 50 pg/mL. FIGS. 19A-19C shows the linearity for Novolog/Novorapid® (insulin aspart) in solvent standards from 50 pg/mL to 500 ng/mL.

Figure 20A:
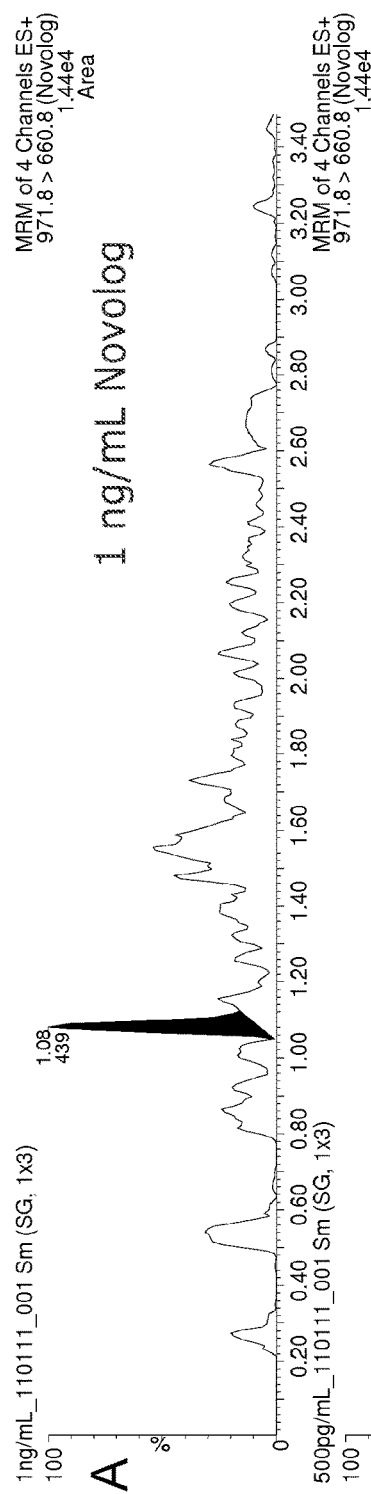
FIGS. 20A-20C shows chromatograms for injections for Novolog/Novorapid® (insulin aspart) extracted from human plasma and analyzed in accordance with the technology.
Figure 20B:
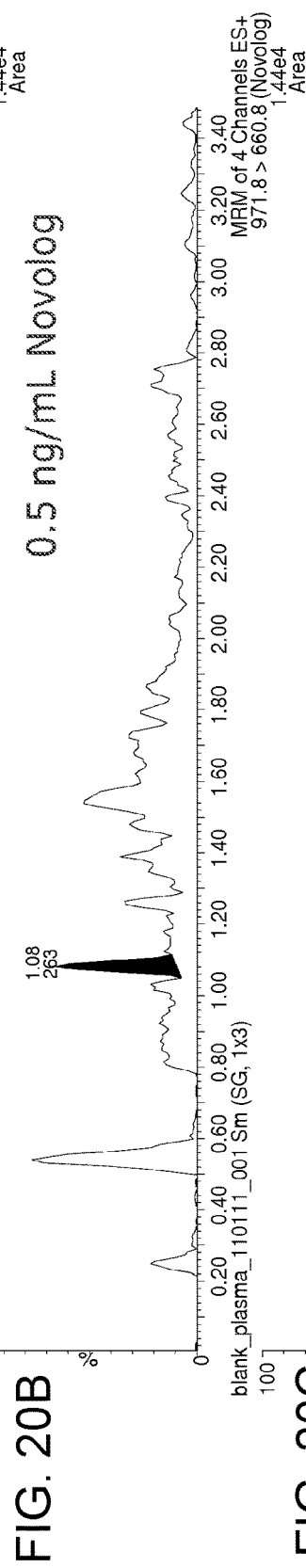
Figure 20C:
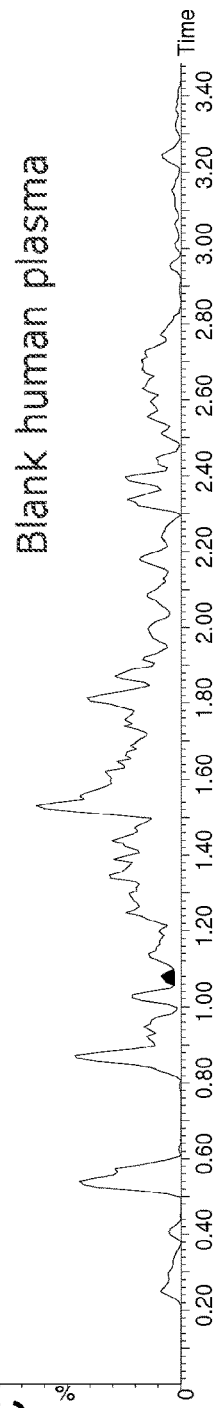
Figure 22A:
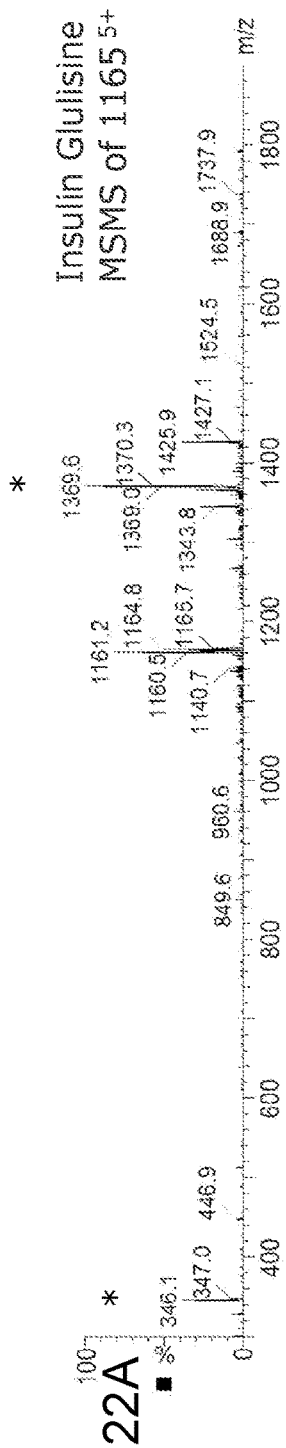
FIGS. 22A-22D shows representative MSMS spectra for insulin analogs.
Figure 22B:
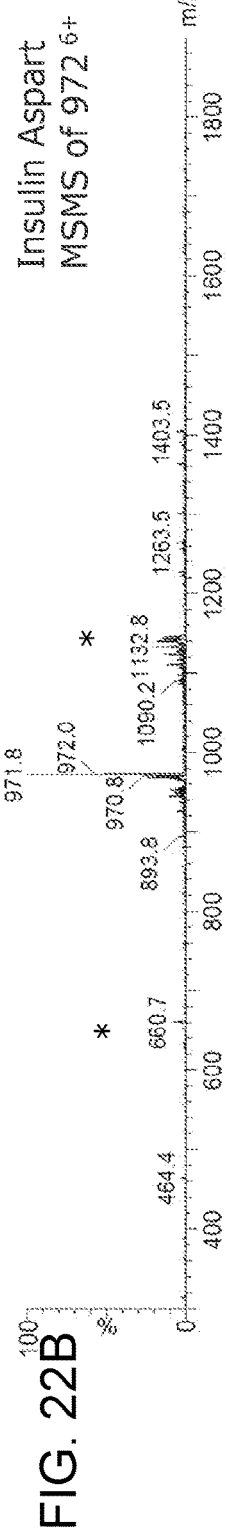
Figure 22C:
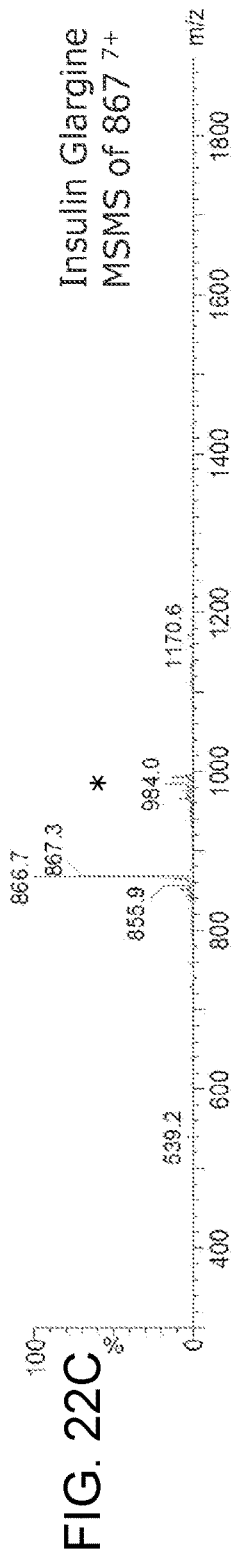
Figure 22D:
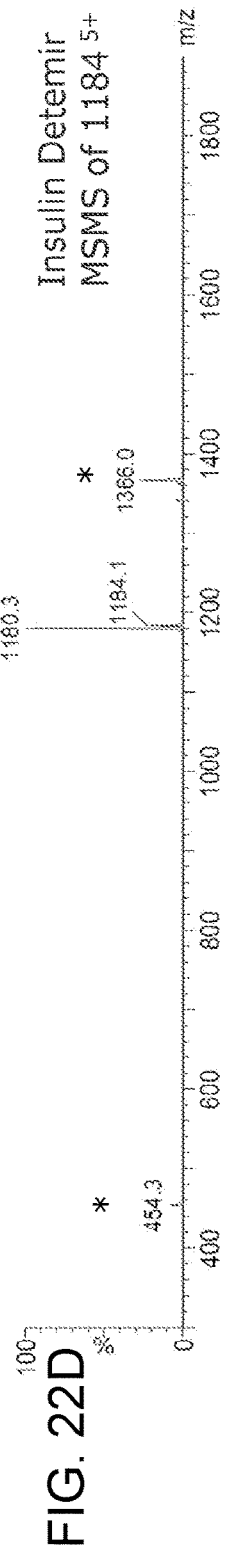

FIG. 20A shows chromatograms for injections of 1 ng/mL (top panel) and 0.5 ng/mL (middle panel), FIG. 20B of Novolog/Novorapid® (insulin aspart) extracted from human plasma and analyzed in accordance with the methods described above. A blank of human plasma is also shown for comparison (bottom panel), FIG. 20C.

Example 5

Human Plasma

A 250 µL sample of plasma is obtained from a human subject. Treatment and extraction of the sample is carried out on a Waters Oasis® HLB micro elution 96-well plate designed for solid phase extraction and having a hydrophilic-lipophilic-balanced reversed-phase sorbent and conditioned with 200 µL methanol equilibrated with 200 µL water. The plasma sample is diluted with 250 µL 10 mM TRIS base (2-amino-2-hydroxymethyl-propane-1,3-diol) and then loaded onto the plate. The plate is washed with 200 µL 5% methanol, 1% acetic acid in water and eluted with 2×25 µL 60% methanol, 10% acetic acid in water and diluted with 50 µL water. Recovery ranges from 50-100%.

Separation is carried out on an ultra high performance liquid chromatography apparatus with a flow-through needle using an ultra high-performance liquid chromatography column (ACQUITY CSH™ 2.1×50 mm, 1.7 µm) wherein the chromatographic surface includes a hydrophobic surface group and one or more ionizable modifiers using the following parameters—Mobile Phase A: 0.1% formic acid in water; Mobile Phase B: 0.1% formic acid in acetonitrile; Weak Wash: mobile phase A; Strong Wash: 50/25/24/1 ACN/IPA/water/formic acid; Flow rate: 0.3 mL/min; Column temperature: 45° C.; Sample Manager temperature: 15° C.; Gradient: 20% B to 65% B in 2 min, to 98% B at 2.1 min, hold for 0.5 min, return to initial at 2.7 min; Total cycle time: 3.5 min, and Injection volume: 10 µL.

MS analysis is carried out on a triple quadrupole MS using the following parameters—Capillary: 3.00 kV; Desolvation temperature: 600° C.; Desolvation flow: 1000 L/hr.

The MRM transitions are optimized according to the analyte of interest. For instance, the analyte of interest can be exenatide, hepcidin, teriparatide, enfuvirtide, calcitonin, brain natriuretic peptide (BNP), amyloid beta peptides, GLP-1, glucagon, or bombesin. The limit of detection for the analyte of interest can be less than 0.2 to 0.5 ng/mL, of instance the limit of detection can be 50 pg/mL. In some embodiments, the limit of detection for the analyte of interest can be less than 30 pg/mL, or can be less than 15 pg/mL.

Analysis of human insulin used the MRM transitions shown in Table 6 below:

TABLE 6

MRM transitions for human insulin

| MRM Transition | Cone Voltage (V) | Collision Energy (eV) |
|---|---|---|
| 969 → 652 | 50 | 25 |
| 969-1130 | 50 | 23 |

Example 6

Human Plasma Standard Curve and Quality Control Data

Linear dynamic range and assay accuracy and precision were determined using standard curves and quality control (QC) samples prepared in human plasma spiked with a mixture of the insulin analogs and a constant concentration of an internal standard. Calibration standards used for quantitation of the various insulins ranged from 0.2 to 25 ng/ml. Using a 1/x weighting and linear fit, the $r^2$ values for all curves, for all insulin analogs were >0.997. The mean accuracy for all standard curve points extracted from human plasma was 93.4%, 91.6%, 96%, and 95.1% for glargine, detemir, aspart, and glulisine, respectively. QC samples were prepared in triplicate in pooled human plasma, as previously described, at 0.35, 0.75, 2, 8, and 20 ng/ml. The mean accuracy for all QC samples was 94.2%, 94.6%, and 91.5% for glargine, detemir, and glulisine, respectively. Representative standard curve and QC statistics are presented in Tables 7 and 8, below. Representative chromatograms of an extracted plasma blank and insulin glulisine at the LOD and LLOQ are shown in FIGS. 23A-23C.

TABLE 7

Representative standard curve and QC sample statistics (n = 3) for insulin detemir from 200 pg/mL to 25 ng/mL in human plasma

| Name | Conc ng/mL | Area | Peak Area Ratio | IS Area | % Dev | Calc Conc ng/mL |
|---|---|---|---|---|---|---|
| Blank plasma | | 31.5 | | | | |
| 200 pg/mL plasma | 0.2 | 153.3 | 0.012 | 13239.5 | 16.6 | 0.23 |
| 500 pg/mL plasma | 0.5 | 375.6 | 0.03 | 12437.3 | −4.6 | 0.48 |
| 1 ng/mL plasma | 1 | 750.2 | 0.06 | 12419.1 | −12.7 | 0.87 |
| 5 ng/mL plasma | 5 | 4714.5 | 0.399 | 11801.8 | 6.3 | 5.31 |
| 10 ng/mL plasma | 10 | 8984.8 | 0.696 | 12907.3 | −8 | 9.20 |
| 25 ng/mL plasma | 25 | 25007.1 | 1.948 | 12836.3 | 2.4 | 25.60 |
| QC 350 pg/mL plasma | 0.35 | 241.6 | 0.02 | 12200.7 | −2.6 | 0.34 |
| QC 750 pg/mL plasma | 0.75 | 733.6 | 0.058 | 12560.6 | 12.9 | 0.85 |
| QC 2 ng/mL plasma | 2 | 1969.4 | 0.141 | 13954.4 | −3.5 | 1.93 |
| QC 8 ng/mL plasma | 8 | 7486.7 | 0.615 | 12168.7 | 1.8 | 8.14 |
| QC 20 ng/mL plasma | 20 | 20549.6 | 1.616 | 12712.9 | 6.3 | 21.26 |

TABLE 8

Representative standard curve and QC sample statistics (n = 3) for insulin glulisine from 200 pg/mL to 25 ng/mL in human plasma

| Name | Conc ng/mL | Area | Peak Area Ratio | IS Area | % Dev | Calc Conc ng/mL |
|---|---|---|---|---|---|---|
| Blank plasma | | 36.9 | | | | |
| 200 pg/mL plasma | 0.2 | 230.3 | 0.013 | 17486.8 | 7.4 | 0.22 |
| 500 pg/mL plasma | 0.5 | 1017.4 | 0.057 | 17807.0 | 5 | 0.53 |
| 1 ng/mL plasma | 1 | 2068.0 | 0.12 | 17249.8 | −3.2 | 0.97 |
| 5 ng/mL plasma | 5 | 11330.0 | 0.61 | 18563.8 | −11.4 | 4.43 |
| 10 ng/mL plasma | 10 | 23803.2 | 1.396 | 17051.6 | −0.2 | 9.98 |
| 25 ng/mL plasma | 25 | 57342.0 | 3.606 | 15903.8 | 2.3 | 25.58 |
| QC 350 pg/mL plasma | 0.35 | 626.1 | 0.035 | 17654.8 | 6.3 | 0.37 |
| QC 750 pg/mL plasma | 0.75 | 1700.4 | 0.101 | 16856.5 | 11.2 | 0.83 |
| QC 2 ng/mL plasma | 2 | 4744.9 | 0.31 | 15317.0 | 15.5 | 2.31 |
| QC 8 ng/mL plasma | 8 | 18609.8 | 1.013 | 18366.4 | −9 | 7.28 |
| QC 20 ng/mL plasma | 20 | 47779.3 | 2.828 | 16894.6 | 0.5 | 20.09 |

CONCLUSIONS

The limit of detection for all 4 insulin analogs was at least 50 pg/mL in solvent standards. The detection or quantitation limit of at least 0.2 to 0.5 ng/mL was achieved for all 4 insulin analogs extracted from 250 µL human plasma.

Recitation of ranges of values herein is merely intended to serve as a shorthand method of referring individually to each separate value falling within the range. Unless otherwise indicated, each individual value is incorporated into the specification as if it were individually recited. Each of the documents cited herein (including all patents, patent applications, scientific publications, manufacturer's specifications, and instructions), are hereby incorporated by reference in their entirety.

The specification should be understood as disclosing and encompassing all possible permutations and combinations of the described aspects, embodiments, and examples unless the context indicates otherwise. One of ordinary skill in the art will appreciate that the technology can be practiced by other than the summarized and described aspect, embodiments, and examples, which are presented for purposes of illustration and not limitation.

The invention claimed is:

1. A method for identifying a polypeptide in a specimen, the method comprising:
   treating a specimen comprising an amount of a polypeptide with a base to form a treated specimen;
   extracting a first fraction of the treated specimen by solid phase extraction using a mixed mode or reversed-phase media and a first solvent comprising an acid;
   separating a component of the first fraction by liquid chromatography using a chromatographic surface material comprising a hydrophobic surface group and one or more ionizable modifiers, and a second solvent comprising an acid, wherein the component of the first fraction comprises undigested polypeptide; and
   analyzing the component of the first fraction by mass spectroscopy to identify the polypeptide in the specimen.

2. The method of claim 1, wherein the hydrophobic surface group comprises a carbon bonded phase.

3. The method of claim 1, wherein the hydrophobic surface group comprises an embedded polar group.

4. The method of claim 1, wherein liquid chromatography uses a chromatographic core material in addition to the chromatographic surface material.

5. The method of claim 4, wherein the chromatographic core material comprises a silica material.

6. The method of claim 4, wherein the chromatographic core material comprises a hybrid inorganic/organic material.

7. The method of claim 4, wherein the chromatographic core material comprises a superficially porous material.

8. The method of claim 4, wherein the chromatographic core material comprises a monolith.

9. The method of claim 1, wherein the base comprises 2-amino-2-hydroxymethyl-propane-1,3-diol.

10. The method of claim 1, wherein treating the specimen further comprises an organic precipitation.

11. The method of claim 1, wherein the mixed mode media comprises ion exchange moieties and reverse phase moieties.

12. The method of claim 1, wherein the first solvent comprises acetic acid.

13. The method of claim 1, wherein the second solvent comprises formic acid.

14. The method of claim 1, wherein the component of the first fraction is analyzed by triple quadrupole mass spectrometry.

15. The method of claim 14, wherein the component of the first fraction is analyzed by triple quadrupole mass spectrometry carried out in positive electrospray ionization mode.

16. The method of claim 1, wherein the polypeptide has a detection limit of 0.25 ng/mL or less.

17. The method of claim 1, wherein analyzing the component of the first fraction by mass spectroscopy can resolve any two or more of insulin glargine, insulin detemir, insulin aspart, insulin glulisine, human insulin, or a derivative or analog thereof.

18. The method of claim 1, wherein analyzing the component of the first fraction by mass spectroscopy can resolve any two or more of exenatide, hepcidin, teriparatide, enfuvirtide, calcitonin, brain natriuretic peptide (BNP), amyloid beta peptides, GLP-1, glucagon, bombesin, or a derivative or analog thereof.

19. A method for assessing the bioequivalence of a first polypeptide and a second polypeptide, the method comprising:
  obtaining a specimen from a bioequivalence assay for a first polypeptide;
  treating the specimen with a base to form a treated specimen;
  extracting a first fraction of the treated specimen by solid phase extraction using a mixed mode or reversed-phase media and a first solvent comprising an acid;
  separating a component of the first fraction by liquid chromatography using a chromatographic surface material comprising a hydrophobic surface group and one or more ionizable modifiers, and a second solvent comprising an acid, wherein the component of the first fraction comprises undigested polypeptide;
  analyzing the component of the first fraction by mass spectroscopy to determine a quantity of the first polypeptide; and
  comparing the quantity of the first polypeptide to a quantity of the second polypeptide expected in a bioequivalence assay for a first polypeptide, thereby determining if the first polypeptide and second polypeptide are bioequivalent.

20. The method of claim 19, wherein bioequivalence is determined based upon an absence of a significant difference in rate and extent to which the first polypeptide and second polypeptide become available at a site of drug action when administered at an identical molar dose under similar conditions in the bioequivalence assay.

21. The method of claim 19, wherein the bioequivalence assay comprises a pharmacokinetic study.

22. The method of claim 19, wherein the bioequivalence assay comprises a pharmacodynamics study.

23. The method of claim 19, wherein the bioequivalence assay comprises a clinical trial.

24. The method of claim 19, wherein the bioequivalence assay comprises an in vitro test.

25. The method of claim 19, wherein the first polypeptide and the second polypeptide are each independently insulin glargine, insulin detemir, insulin aspart, insulin glulisine, human insulin, or a derivative or analog thereof.

26. The method of claim 19, wherein the first polypeptide and the second polypeptide are each independently exenatide, hepcidin, teriparatide, enfuvirtide, calcitonin, brain natriuretic peptide (BNP), amyloid beta peptides, GLP-1, glucagon, bombesin, or a derivative or analog thereof.

27. The method of claim 19, wherein liquid chromatography uses a chromatographic core material in addition to the chromatographic surface material.

28. The method of claim 27, wherein the chromatographic core material comprises a hybrid inorganic/organic material.

* * * * *